United States Patent
Yasuma et al.

(10) Patent No.: US 6,552,054 B1
(45) Date of Patent: Apr. 22, 2003

(54) CHROMONE DERIVATIVES, PROCESS FOR THE PREPARATION OF THE SAME AND USES THEREOF

(75) Inventors: Tsuneo Yasuma, Ibaraki (JP); Masahiro Kawase, Hyogo (JP); Akira Mori, Kyoto (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 10/070,150

(22) PCT Filed: Aug. 31, 2000

(86) PCT No.: PCT/JP00/05910

§ 371 (c)(1), (2), (4) Date: Mar. 1, 2002

(87) PCT Pub. No.: WO01/16127

PCT Pub. Date: Aug. 3, 2001

(30) Foreign Application Priority Data

Sep. 1, 1999 (JP) .............................. 11-247418

(51) Int. Cl.⁷ ...................... A61K 31/425; A61K 31/42; A61K 31/35
(52) U.S. Cl. ..................... 514/365; 514/233.5; 514/320; 514/376; 514/456; 549/402; 548/183; 548/192; 548/215; 548/226; 546/196; 544/151
(58) Field of Search .......................... 549/402; 544/151; 548/183, 192, 215, 226; 514/456, 233.5, 376, 365, 320; 546/196

(56) References Cited

FOREIGN PATENT DOCUMENTS

JP 256358 9/2000
WO WO 00/06550 2/2000

OTHER PUBLICATIONS

Raposo, Cesar; Almaraz, Marta; Martin, Mercedes; Alcazar, Victoria; Caballero, Ma Crus; Moran, Joaquin R. 'The effect of chromenone receptors on the selectivity of the reaction between pyrrolidine and 5–hydroxymethyl–2(5H)–furanone' 1997.*

Sohda, Takashi; Taketomi, Shigehisa; Oda, Tsuneo 'Benzopyran derivatives and their use' 1995.*

* cited by examiner

Primary Examiner—Amelia Owens
(74) Attorney, Agent, or Firm—Mark Chao; Elaine M. Ramesh

(57) ABSTRACT

The invention provides chromone derivatives of the following general formula, a process for preparing such chromone derivatives and a prophylactic and therapeutic agent comprising such chromone derivatives for bone diseases and chondropathy:

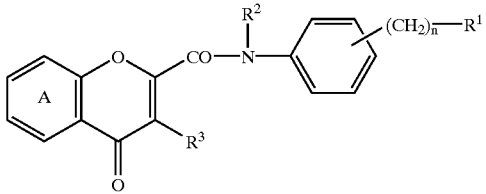

wherein the ring A is an optionally substituted benzene ring; $R^1$ is an optionally substituted non-aromatic heterocyclic group; $R^2$ is a hydrogen atom or hydrocarbon group; $R^3$ is a hydrogen atom, hydrocarbon group or halogen; n is an integer of 0–3; or a salt thereof.

18 Claims, No Drawings

CHROMONE DERIVATIVES, PROCESS FOR THE PREPARATION OF THE SAME AND USES THEREOF

This application is the National Stage of International Application No. PCT/JP00/05910, filed on Aug. 31, 2000.

TECHNICAL FIELD

The present invention relates to chromone derivatives having an osteogenesis promoting effect, their production and use.

BACKGROUND OF THE INVENTION

Osteoporosis is a pathological state or disorder in which certain symptoms or risks occur due to a decrease in bone quantity that has reached a certain level. For example, a major symptom of it, is kyphosis, and a fracture in thoracic and lumbar vertebrae and vertebral bodies, femoral neck, distal extremity of radius, costa, proximal extremity of humerus, and the like. In osseous tissue, bone formation and destruction by bone resorption occur continuously, with a balance between them being kept, and osteoblasts in osteogenesis and osteoclasts in bone resorption play a central role in that. Loss of the balance between bone formation and bone resorption results in osteoporosis accompanied by a decrease in quantity of the bone.

Conventionally, as preventive or therapeutic agents, bone resorption-suppressing substances such as estrogens, calcitonins, bisphoshonates, and the like have primarily been used. When these bone resorption-suppression agents are given, however, in some cases, the patients to whom the agents can be administered are limited, or the effect is uncertain, and no sufficient effect is attained. Accordingly, it is desirable to develop osteogenesis promoting agents, which increase the decreased bone quantity actively as preventive or therapeutic agents for osteoporosis.

Benzopyran derivatives having an osteogenesis promoting effect are disclosed in Japanese Unexamined Patent Publication No. (hereinafter referred to as JP-A 7-291983).

BRIEF SUMMARY OF THE INVENTION

The present invention provides chromone derivatives having an excellent osteogenesis promoting effect, the production thereof and osteogenesis promoting agents containing them as effective components. The present inventors worked diligently to investigate and develop a compound having an osteogenesis promoting effect and they discovered that chromone derivatives having a non-aromatic heterocyclic group have a prominent osteogenesis promoting effect. The present inventors made further investigations based on these findings and succeeded in establishing the present invention.

That is, the present invention relates to:
(1) a chromone derivative of the formula:

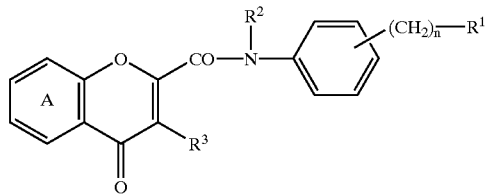

wherein the ring A is an optionally substituted benzene ring; $R^1$ is an optionally substituted non-aromatic heterocyclic group; $R^2$ is a hydrogen atom or a hydrocarbon group; $R^3$ is a hydrogen atom, a hydrocarbon group or halogen; n is an integer of 0 to 3; or a salt thereof, (2) a compound described in the above item (1), wherein the ring A is a benzene ring which may be substituted by 1 to 3 substituents selected from the group consisting of hydroxy, acyloxy, mercapto, halogen atom, $C_{1-10}$ alkyl, $C_{1-10}$ alkoxy, $C_{1-10}$ alkylthio and alkylenedioxy of the formula: —O—$(CH_2)_m$—O— (wherein m is an integer of 1–4); $R^2$ is a hydrogen atom or a $C_{1-6}$ alkyl; and $R^3$ is a hydrogen atom; or a salt thereof, (3) a compound described in the above item (1), wherein a substructure containing the ring A is represented by the formula:

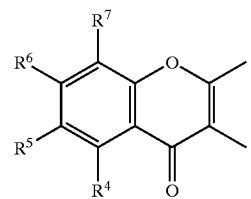

(wherein $R^4$ is a hydrogen atom or a hydroxy group, each of $R^5$ to $R^7$ may be same or different and each is a hydrogen atom, a halogen atom, a $C_{1-10}$ alkyl or a $C_{1-10}$ alkoxy), $R^2$ is a hydrogen atom or a $C_{1-6}$ alkyl group; $R^3$ is a hydrogen atom, or a salt thereof, (4) a compound as described in the above item (1), wherein the non-aromatic heterocyclic group of the optionally substituted non-aromatic heterocyclic group represented by $R^1$ is a 5- to 7-membered non-aromatic heterocyclic group containing from 1 to 4 heteroatoms selected from the group consisting of nitrogen atom, sulfur atom and oxygen atom, or a salt thereof, (5) a compound as described in the above item (4), wherein the 5- to 7-membered non-aromatic heterocyclic group of the optionally substituted 5- to 7-membered non-aromatic heterocyclic group is one containing at least 1 nitrogen atom, or a salt thereof, (6) a compound as described in the above item (5), wherein the 5- to 7-membered non-aromatic heterocyclic group of the optionally substituted 5- to 7-membered non-aromatic heterocyclic group is pyrrolidine, imidazolidine, thiazolidine, isothiazolidine, oxazolidine, oxadiazolidine, piperidine, piperazine, thiomorpholine or morpholine, or a salt thereof, (7) a compound as described in the above item (1), wherein the substituents in the optionally substituted non-aromatic heterocyclic group represented by $R^1$ are 1 to 4 substituents selected from the group consisting of halogen atom, hydroxy, oxo, $C_{1-10}$ alkyl, $C_{1-6}$ alkoxy, $C_{1-6}$ acyl, amino, mono- or di-$C_{1-6}$ alkylamino, $C_{1-6}$ alkylsulfonyl, carboxy, $C_{1-6}$ alkoxy-carbonyl or phosphono, or a salt thereof, (8) a compound as described in the above item (3), wherein $R^2$ is a hydrogen atom and $R^4$ is a hydroxy group, or a salt thereof, (9) a compound as described in the above item (3), wherein $R^2$ and $R^4$ are each a hydrogen atom, or a salt thereof,

(10) a prodrug of the compound as described in the above item (1),

(11) N-4-(2,4-dioxothiazolidin-5-yl)methyl]phenyl]-4-oxo-4H-1-benzopyran-2-carboxamide, N-[4-[(2,4-dioxo-oxazolidin-5-yl)methyl]phenyl]-4-oxo-4H-1-benzopyran-2-carboxamide, N-[4-[(4-morpholinyl)methyl]phenyl]-4-oxo-4H-1-benzopyran-2-carboxamide, 5,7-dihydroxy-N-[4-(2,4-dioxothiazolidin-5-yl)methyl]
phenyl]-4-oxo-4H-1-benzopyran-2-carboxamide, N-[4-
[2,4-dioxothiazolidin-5-yl]methyl]phenyl]-5-hydroxy-7-
methoxy-4-oxo-4H-1-benzopyran-2-carboxamide, 5,7-
dihydroxy-N-[4-[(4-morpholinyl)methyl]phenyl]-4-oxo-
4H-1-benzopyran-2-carboxamide, 5-hydroxy-N-[4-[(4-
morpholinyl)methyl]phenyl]-4-oxo-4H-1-benzopyran-2-
carboxamide, N-[4-[(2-oxazolidon-3-yl)methyl]phenyl]-
4-oxo-4H-1-benzopyran-2-carboxamide, N-[4-(2,6-
dioxo-1-piperidinyl)methyl]phenyl]-4-oxo-4H-1-
benzopyran-2-carboxamide, N-[4-(2,4-dioxo-oxazolidin-
5-yl)methyl]phenyl]-5-hydroxy-4-oxo-4H-1-benzopyran-
2-carboxamide, 5-hydroxy-N-methyl-N-[4-(4-
morpholinyl)methyl]phenyl]-4-oxo-4H-1-benzopyran-2-
carboxamide, or 4-oxo-N-[4-[(4-oxo-1-piperidinyl)
methyl]phenyl]-4H-1-benzopyran-2-carboxamide, or a
salt thereof,

(12) A process for producing chromone derivatives of the
formula:

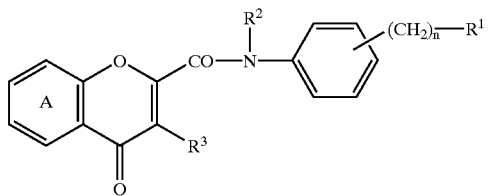

wherein the ring A is an optionally substituted benzene
ring; $R^1$ is an optionally substituted non-aromatic het-
erocyclic group; $R^2$ is a hydrogen atom or a hydrocar-
bon group; $R^3$ is a hydrogen atom, a hydrocarbon
group, or a halogen; and n is an integer of 0–3; or a salt
thereof, which comprises reacting a compound of the
formula:

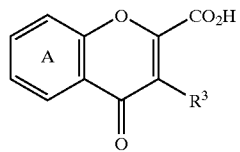

wherein each symbol has the same meaning as mentioned
above; or a reactive derivative at the carboxy group
thereof or a salt thereof, with a compound of the
formula:

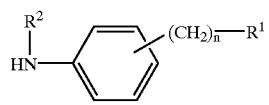

wherein each symbol has the same meaning as mentioned
above; or a reactive derivative at the amino group
thereof or a salt thereof,

(13) 5,6-methylenedioxy-4-oxo-4H-1-benzopyran-2-
carboxylic acid, 5,6-dihydroxy-4-oxo-4H-1-benzopyran-
2-carboxylic acid, or 5-hydroxy-7-methyl-4-oxo-4H-1-
benzopyran-2-carboxylic acid; or a salt thereof,

(14) a pharmaceutical composition which comprises a com-
pound of the formula:

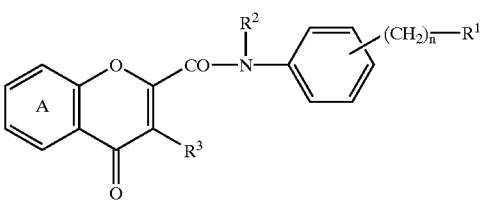

wherein the ring A is an optionally substituted benzene
ring; $R^1$ is an optionally substituted non-aromatic het-
erocyclic group; $R^2$ is a hydrogen atom or a hydrocar-
bon group, $R^3$ is a hydrogen atom, a hydrocarbon
group, or halogen; and n is an integer of 0–3; or a salt
thereof,

(15) a pharmaceutical composition according to the above
item (14), which is an osteogenesis promoting agent,

(16) a pharmaceutical composition according to the above
item (14), which is a prophylactic or therapeutic agent for
bone diseases,

(17) a pharmaceutical composition according to the above
item (14), which is a prophylactic or therapeutic agent for
fracture,

(18) a pharmaceutical composition according to the above
item (14), which is a prophylactic or therapeutic agent for
chondropathy.

(19) a pharmaceutical composition which comprises a pro-
drug described in the above item (10),

(20) a method for promoting osteogenesis which comprises
administering a compound described in the above item (1)
or a salt thereof, and

(21) Use of a compound described in the above item (1) or
a salt thereof for manufacturing an osteogenesis promot-
ing agent.

DETAILED DESCRIPTION OF THE INVENTION

In the above mentioned formulae, as for the substituent on
the optionally substituted benzene ring represented by the
ring A, for example, halogen atom, nitro, optionally substi-
tuted alkyl group, optionally substituted hydroxy group,
optionally substituted mercapto group, optionally substi-
tuted amino group, acyl group, mono- or
di-alkoxyphosphoryl group, phosphono group, optionally
substituted aryl group, optionally substituted aralkyl group,
or optionally substituted aromatic heterocyclic group may be
used, and these may be the same or different, of which 1 to
4, preferably 1 to 3, may be substituted on the benzene ring.

The "halogen atom" includes, for example, fluorine,
chlorine, bromine and iodine.

The alkyl group of the "optionally substituted alkyl
group" includes, preferably, alkyl of 1–10 carbon atoms,
e.g., methyl, ethyl, propyl, isopropyl, butyl, sec-butyl, tert-
butyl, pentyl, isopentyl, neopentyl, hexyl, heptyl, octyl,
nonyl, decyl, and the like, and cycloalkyl of 3–7 carbon
atoms, e.g., cyclopropyl, cyclobutyl, cyclohexyl or
cycloheptyl, and the like, which may be substituted by 1 to
3 substituents such as, for example, halogen atom, e.g.,
fluorine, chlorine, bromine, iodine, etc., hydroxy, alkoxy
group of 1–6 carbon atoms, e.g., methoxy, ethoxy, propoxy,
butoxy, hexyloxy, etc., mono- or di-($C_{1-6}$alkoxy)
phosphoryl group, e.g., methoxyphosphoryl,
ethoxyphosphoryl, dimethoxyphosphoryl,
di-ethoxyphosphoryl, etc., phosphono, and the like.

The substituted alkyl group is exemplified by tri-
fluoromethyl, trifluoroethyl, trichloromethyl, hydroxymethyl, 2-hydroxyethyl, 1-methoxyethyl, 2-methoxyethyl, 2,2-diethoxyethyl, 2-diethoxyphosphorylethyl, phosphonomethyl, and the like.

The substituted hydroxy group in the "optionally substituted hydroxy group" includes alkoxy group, alkenyloxy group, aralkyloxy group, acyloxy group, aryloxy group, and the like. The "alkoxy group" includes, preferably, alkoxy group of 1–10 carbon atoms, e.g., methoxy, ethoxy, propoxy, butoxy, tert-butoxy, pentyloxy, hexyloxy, heptyloxy, nonyloxy, and the like, and cycloalkoxy group of 4–6 carbon atoms, e.g., cyclobutoxy, cyclopentoxy, cyclohexyloxy, and the like. The "alkenyloxy group" includes, preferably, those of 2–10 carbon atoms, e.g., allyloxy, crotyloxy, 2-pentenyloxy, 3-hexenyloxy, 2-cyclopentenylmethoxy, 2-cyclohexenylmethoxy, and the like. The "aralkyloxy group" includes, preferably, those of 7–19 carbon atoms, more preferably $C_{6-14}$ aryl-$C_{1-4}$ alkyloxy, e.g., benzyloxy, phenethyloxy, and the like. The "acyloxy group" includes, preferably, alkanoyloxy group, carbamoyloxy group, alkoxylcarbonyloxy group, preferably $C_{1-10}$ alkoxylcarbonyloxy, and the like. The "acyloxy group" includes, preferably, alkanoyloxy group, for example, those of 2–10 carbon atoms, e.g., acetyloxy, propionyloxy, n-butyryloxy, i-butyryloxy, hexanoyloxy, and the like. The "carbamoyloxy group" mentioned in the above includes, not only a carbamoyloxy group, but an optionally substituted carbamoyloxy group as well, for example, carbamoyloxy group substituted by 1 or 2 alkyl groups. The alkyl group in the carbamoyloxy group substituted by 1 or 2 alkyl groups includes alkyl group of 1–10 carbon atoms, e.g., methyl, ethyl, propyl, isopropyl, butyl, isobutyl, sec-butyl, tert-butyl, pentyl, isopentyl, neopentyl, hexyl, heptyl, octyl, nonyl, decyl, and the like, cycloalkyl group of 3–7 carbon atoms, e.g., cyclopropyl, cyclobutyl, cyclohexyl, cycloheptyl, and the like, and preferably alkyl group of 1–6 carbon atoms. The "carbamoyloxy group" mentioned in the above includes, preferably, carbamoyloxy, methylcarbamoyloxy, dimethylcarbamoyloxy, ethylcarbamoyloxy, and diethylcarbamoyloxy, and the like. The "allyloxy group" includes, allyloxy group of 6–14 carbon atoms, e.g., phenoxy, biphenyloxy. These groups may be substituted by 1 to 3 substituents such as, for example, halogen atom mentioned in the above, hydroxy, alkoxy group of 1–6 carbons, mono- or di-($C_{1-6}$alkoxy) phosphoryl group, phosphono group, and the like. The substituted hydroxy group is exemplified by trifluoromethoxy, 2,2,2-trifluoroethoxy, difluoromethoxy, 2-methoxyethoxy, 4-chlorobenzyloxy, 2-(3,4-dimethoxyphenyl)ethoxy, methoxy, methylenedioxy, acetyloxy, n-butyryloxy, i-butyryloxy, diethylcarbamoyloxy, and the like.

The mercapto group in the "optionally substituted mercapto group" includes, mercapto group substituted by the same group as the substituent of "optionally substituted hydroxy group" described above, and for example, alkylthio group, aralkylthio group, acylthio group, and the like. The alkylthio group includes, preferably, alkylthio group of 1–10 carbon atoms, e.g., methylthio, ethylthio, propylthio, butylthio, pentylthio, hexylthio, heptylthio, nonylthio, and the like, and cycloalkylthio group of 4–6 carbon atoms, e.g., cyclobutylthio, cyclopentylthio, cyclohexylthio, and the like. The "aralkylthio group" includes, preferably, those of 7–19 carbon atoms, more preferably, $C_{6-14}$-aryl-$C_{1-4}$ alkylthio, e.g., benzylthio, phenethylthio, and the like. The "acylthio group" includes, preferably, alkanoylthio, for example, those of 2–10 carbon atoms, e.g., acetylthio, propionylthio, n-butyrylthio, hexanoylthio, and the like. These groups may further be substituted by 1–3 substituents such as, for example, the above-mentioned halogen atom, hydroxy group, alkoxy group of 1–6 carbon atoms, mono- or di-($C_{1-6}$ alkoxy) phosphoryl group, phosphono group, and the like. The substituted thiol group is exemplified by trifluoromethylthio, 2,2,2-trifluoroethylthio, 2-methoxyethylthio, 4-chlorobenzylthio, 3,4-dichlorobenzylthio, 4-fluorobenzylthio, 2-(3,4-dimethoxyphenyl) ethylthio, and the like.

The substituent of the substituted amino group in the "optionally substituted amino group" includes the above-mentioned alkyl group of 1–10 carbon atoms, alkenyl group of 2–10 carbon atoms, e.g., allyl, vinyl, 2-penten-1-yl, 3-penten-1-yl, 2-hexen-1-yl, 3-hexen-1-yl, 2-cyclohexenyl, 2-cyclopentenyl, 2-methyl-2-propen-1-yl, 3-methyl-2-buten-1-yl, and the like, aryl group of 6–14 carbon atoms, and aralkyl group of 7–19 carbon atoms, and these may be used alone or as two identical or different groups. These groups may be substituted by the above-mentioned halogen atom, alkoxy group of 1–6 carbon atoms, mono- or di-($C_{1-6}$ alkoxy) phosphoryl group, phosphono, and the like. The substituted amino acid group is exemplified by methylamino, dimethylamino, ethylamino, diethylamino, dibutylamino, diallylamino, cyclohexylamino, phenylamino, or N-methyl-N-phenylamino, N-methyl-N-(4-chlorobenzyl)amino, N,N-di-(2-methoxyethyl)amino, and the like.

The "acyl group" includes an organic carboxylic acyl group, sulfonic acyl group having a hydrocarbon group of 1–6 carbon atoms (e.g., methyl, ethyl, n-propyl, hexyl, phenyl, etc.), carbamoyl group, and the like. The "organic carboxylic acyl group" used includes, for example, formyl, alkyl-carbonyl group of 1–10 carbon atoms, e.g., acetyl, propionyl, butyryl, valeryl, pivaloyl, hexanoyl, octanoyl, cyclobutanecarbonyl, cyclohexanecarbonyl, cycloheptanecarbonyl, etc., alkenyl-carbonyl group of 2–10 carbon atoms, e.g., crotonyl, 2-cyclohexenecarbonyl, etc., aryl-carbonyl group of 6–14 atoms, e.g., benzoyl, etc., aralkyl-carbonyl group of 7–19 carbon atoms, e.g., benzylcarbonyl, benzhydrylcarbonyl, etc., 5- or 6-membered aromatic heterocyclic carbonyl group, e.g., nicotinoyl, 4-thiazolyl-carbonyl, etc., 5- or 6-membered aromatic heterocyclic acetyl group, e.g., 3-pyridylacetyl, 4-thiazolylacetyl, etc. The "sulfonic acyl group having a hydrocarbon group of 1–6 carbon atoms" includes, for example, alkane sulfonyl group of 1–6 carbon atoms, e.g., methanesulfonyl, ethanesulfonyl, and the like. These groups may further be substituted by 1–3 substituents, for example, the above-mentioned halogen atom, hydroxy, alkoxy group of 1–6 carbon atoms, amino, and the like. The acyl group is exemplified by trifluoroacetyl, trichloroacetyl, 4-methoxybutyryl, 3-cyclohexyloxypropionyl, 4-chlorobenzoyl, 3,4-dimethoxybenzoyl, and the like.

The "carbamoyl group" mentioned in the above includes, not only a carbamoyl group, but an optionally substituted carbamoyl group as well, for example, carbamoyl group substituted by 1 or 2 alkyl groups. The alkyl group in the carbamoyl group substituted by 1 or 2 alkyl groups includes alkyl group of 1–10 carbon atoms, e.g., methyl, ethyl, propyl, isopropyl, butyl, isobutyl, sec-butyl, tert-butyl, pentyl, isopentyl, neopentyl, hexyl, heptyl, octyl, nonyl, decyl, and the like, cycloalkyl group of 3–7 carbon atoms, e.g., cyclopropyl, cyclobutyl, cyclohexyl, cycloheptyl, and the like, and preferably alkyl group of 1–6 carbon atoms. The "carbamoyl group" mentioned in the above includes, preferably, carbamoyl, methylcarbamoyl, dimethylcarbamoyl, ethylcarbamoyl, and diethylcarbamoyl, and the like.

The "mono- or di-alkoxyphosphoryl group" includes mono-$C_{1-6}$ alkoxyphosphoryl groups, such as methoxyphosphoryl, ethoxyphosphoryl, propoxyphosphoryl, isopropoxyphosphoryl, butoxyphosphoryl, pentyloxyphosphoryl, hexyloxyphosphoryl, and the like, and di-$C_{1-6}$ alkoxyphosphoryl groups such as dimethoxyphosphoryl, diethoxyphosphoryl, dipropoxyphosphoryl, diisopropoxyphosphoryl, dibutoxyphosphoryl, dipentyloxyphosphoryl, dihexyloxyphosphoryl, and the like. Preferably, di-$C_{1-6}$ alkoxyphosphoryl groups, for example, dimethoxyphosphoryl, diethoxyphosphoryl, dipropoxyphosphoryl, diisopropoxyphosphoryl, ethylenedioxyphosphoryl, dibutoxyphosphoryl, and the like may be used.

The aryl group in the "optionally substituted aryl group" includes, preferably, those of 6–14 carbon atoms, for example, phenyl, naphthyl, anthryl, and the like. These groups may be substituted by 1–3 substituents such as alkyl group of 1–10 carbon atoms, halogen atom, hydroxy, alkoxy group of 1–6 carbon atoms, and the like. The substituted aryl group is exemplified by 4-chlorophenyl, 3,4-dimethoxyphenyl, 4-cyclohexylphenyl, 5,6,7,8-tetrahydro-2-naphthyl, and the like.

The aralkyl group in the "optionally substituted aralkyl group" includes, preferably, those of 7–19 carbon atoms, for example, benzyl, naphthylethyl, trityl, and the like, and these groups may be substituted on the aromatic ring by 1–3 substituents. such as the above-mentioned alkyl group of 1–10 carbon atoms, halogen atom, hydroxy, alkoxy group of 1–6 carbon atoms, and the like. The substituted aralkyl group is exemplified by 4-chlorobenzyl, 3,4-dimethoxybenzyl, 4-cyclohexylbenzyl, 5,6,7,8-tetrahydro-2-naphthylethyl, and the like.

The aromatic heterocyclic group in the "optionally substituted aromatic heterocyclic group" includes, preferably, 5- or 6-membered ones having 1 to 4 heteroatoms selected from nitrogen, oxygen and/or sulfur, for example, furyl, thienyl, imidazolyl, thiazolyl, oxazolyl, thiadiazolyl, and the like. These groups may be substituted by 1–3 substituents such as the above-mentioned alkyl group of 1–10 carbon atoms, halogen atom, hydroxy, alkoxy group of 1–6 carbon atoms, and the like.

When two alkyl groups are placed adjacent to each other on the benzene ring A, they may be bound to each other to form an alkylene group of the formula: $-(CH_2)_L-$ [wherein L is an integer of 3–5] e.g., trimethylene, tetramethylene, pentamethylene, etc.), and when two alkoxy groups are placed adjacent to each other, they may form an alkylenedioxy group of the formula: $-O-(CH_2)_m-O-$ [wherein m is an integer of 1–4] (e.g., methylenedioxy, ethylenedioxy, trimethylenedioxy, etc.). In such cases, a 5- to 8-membered ring is formed together with the carbon atoms on the benzene ring.

The preferred substituent on the ring A includes, for example, hydroxy group, $C_{2-10}$ alkanoyloxy group, carbamoyloxy group substituted by 1 or 2 $C_{1-10}$ alkyl groups, mercapto group, halogen atom, $C_{1-10}$ alkyl group, $C_{1-10}$ alkoxy group, $C_{1-10}$ alkylthio group, alkylenedioxy group of the formula: $-O-(CH_2)m-O-$ [wherein m is an integer of 1–4], and the like, wherein the number of substituents is preferably 1 to 3.

As the ring A, a group of the following formula is preferred:

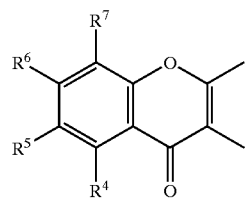

wherein $R^4$ is hydrogen atom or hydroxy group; $R^5$ to $R^7$ are independently hydrogen atom, halogen atom, $C_{1-10}$ alkyl, or $C_{1-10}$ alkoxy; each may be the same or different, For $R^4$ described above, hydrogen atom or hydroxy group are preferred and hydroxy is more preferred.

In the above-mentioned formulae, the non-aromatic heterocycle in the optionally substituted non-aromatic heterocyclic group represented by $R^1$ includes 3- to 8-membered (preferably 5- to 7-membered) ones containing 1 to 4 heteroatoms selected from the group consisting of nitrogen atom, sulfur atom and oxygen atom, preferably, non-aromatic heterocycle wherein the heteroatom is selected from nitrogen atom, sulfur atom and oxygen atom, more preferably, 3- to 8-membered non-aromatic heterocycle, wherein the hetero atom is selected from nitrogen atom, sulfur atom and oxygen atom. Such a heterocycle is exemplified by oxirane, azetidine, oxetane, thietane, pyrrolidine, tetrahydrofuran, thiolane, piperidine, tetrahydropyran, morpholine, thiomorpholine, piperazine, homopiperidine, pyrroline, imidazolidine, thiazoline, isothiazoline, thiazolidine, isothiazolidine, imidazolidine, oxazoline, oxazolidine, oxadiazolidine, oxathiazolidine, dithiazolidine, thiadiazolidine, and the like.

In particular, 5- to 7-membered non-aromatic heterocycles which contain at least a nitrogen atom are preferred, and especially, pyrrolidine, imidazolidine, thiazolidine, isothiazolidine, oxazolidine, oxadiazolidine, piperidine, piperazine, thiomorpholine and morpholine.

In the above-mentioned formulae, the substituent on the optionally substituted non-aromatic heterocyclic group includes, for example, (i) halogen atom (e.g., fluorine, chlorine, bromine, iodine, etc.), (ii) hydroxy or oxo, (iii) $C_{1-10}$ alkyl (e.g., methyl, ethyl, propyl isopropyl, butyl, isobutyl, sec-butyl, tert-butyl, pentyl, neopentyl, hexyl, heptyl, octyl, nonyl, or decyl, etc.), (iv) $C_{1-6}$ alkoxy (e.g., methoxy, ethoxy, propoxy, butoxy, tert-butoxy, pentyloxy, hexyloxy, etc.), (v) $C_{1-6}$ acyl (e.g., acetyl, propionyl, etc.), (vi) amino group optionally substituted by $C_{1-6}$ alkyl (e.g., amino, methylamino, ethylamino, dimethylamino, diethylamino, dipropylamino, etc.), (vii) $C_{1-6}$ alkylsulfonyl, (viii)carboxy, (ix) $C_{1-6}$ alkoxy-carbonyl (e.g., methoxycarbonyl, ethoxycarbonyl, propoxycarbonyl), (x)phosophono, and the like, and the number of substituents is preferably 1 to 4.

The optionally substituted non-aromatic heterocyclic group is exemplified by oxiranyl, azetidinyl oxetanyl, thietanyl, pyrrolidinyl, tetrahydrofuryl, thiolanyl, piperidyl, tetrahydropyranyl, morpholinyl, thiomorpholinyl, piperazinyl, homopiperidyl, 4-oxopiperidyl, pyrrolinyl, imidazolidinyl, 4-formylpiperazinyl, 4-methanesulfonylpiperazinyl, 3-hydroxypyrrolidinyl, 2,4-dioxothiazolidin-5-yl, 2,4-dioxothiazolidin-3-yl, hydantoin-3-yl, glutarimido-4-yl, 1-methylhydantoin-3-yl, succinimido, 2-oxazolidon-3-yl, 2,4-dioxo-oxazolidin-5-yl, 2,4-dioxo-oxazolidin-3-yl, 1,1-dioxotetrahydro-2H-1-isothiazol-2-yl, 3,5-dioxo-1,2,4-oxadiazolin-2-yl, and the like.

These non-aromatic heterocyclic groups may be condensed with a benzene ring, a 6-membered ring containing 2 or less nitrogen atoms, or a 5-membered ring containing one sulfur atom. The condensed non-aromatic heterocyclic group is exemplified by chromanyl, isochromanyl, indolinyl, isoindolinyl, thiochromanyl, isothiochromanyl, and the like.

As the hydrocarbon group represented by $R^2$ and $R^3$ in the above-mentioned formulae, the same group as mentioned above may be used, that is, alkyl group (preferably, alkyl of 1–10 carbon atoms, e.g., methyl, ethyl, propyl, isopropyl, butyl, isobutyl, sec-butyl, tert-butyl, pentyl, isopentyl, neopentyl, hexyl, and the like), alkenyl group (preferably, alkenyl of 2–10 carbon atoms, e.g., vinyl, aryl, isopropenyl, 2-methylallyl, 1-propenyl, 2-methyl-1-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl and the like), alkynyl group (preferably, alkynyl of 2–10 carbon atoms, e.g., ethynyl, 1-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, and the like), cycloalkyl group (preferably, cycloalkyl of 3–9 carbon atoms, e.g., cyclopropyl, cyclobutyl, cyclopentyl, cyclohexyl, cycloheptyl, cyclooctyl, cyclononyl, and the like), cycloalkenyl group (preferably, cycloalkenyl of 3–6 carbon atoms, e.g., 2-cyclopenten-1-yl, 3-cyclopenten-1-yl, 2-cyclohexen-1-yl, 3-cyclohexen-1-yl, 1-cyclobuten-1-yl, 1-cyclopenten-1-yl, and the like), aryl group (preferably, aryl of 6–14 carbon atoms, e.g., phenyl, 1-naphthyl, 2-naphthyl, anthryl, phenanthryl, acenaphthylenyl, and the like), aralkyl group (preferably, aralkyl of 7–19 carbon atoms, e.g., benzyl, phenethyl, and the like).

As the above-mentioned hydrocarbon groups, for example, a straight or branched $C_{1-6}$ alkyl group such as methyl, ethyl, propyl, isopropyl, butyl, isobutyl, sec-butyl, tert-butyl, pentyl, isopentyl, neopentyl, hexyl, and the like, is preferred. Particularly, a $C_{1-4}$ alkyl group is preferred.

As the above-mentioned group $R^2$, a hydrogen atom or a $C_{1-6}$ alkyl group is preferred, and particularly, a hydrogen atom is preferred.

As the halogen in the above-mentioned group $R^3$, the same halogen atom as mentioned-above is used.

As the above-mentioned group $R^3$, a hydrogen atom is preferred.

In the above-mentioned formulae, n is an integer of 0–3, preferably 1 or 2.

More preferred examples of the present compound are as follows: N-[4-[(2,4-dioxothiazolidin-5-yl)methyl]phenyl]-4-oxo-4H-1-benzopyran-2-carboxamide, N-[4-[(2,4-dioxooxazolidin-5-yl)methyl]phenyl]-4-oxo-4H-1-benzopyran-2-carboxamide, N-[4-[(4-morpholinyl)methyl]phenyl]-4-oxo-4H-1-benzopyran-2-carboxamide, 5,7-dihydroxy-N-[4-[(2,4-dioxothiazolidin-5-yl)methyl]phenyl]-4-oxo-4H-1-benzopyran-2-carboxamide, N-[4-[(2,4-dioxothiazolidin-5-yl)methyl]phenyl]-5-hydroxy-7-methoxy-4-oxo-4H-1-benzopyran-2-carboxamide, 5,7-dihydroxy-N-[4-[(4-morpholinyl)methyl]phenyl]-4-oxo-4H-1-benzopyran-2-carboxamide, 5-hydroxy-N-[4-[(4-morpholinyl)methyl]phenyl]-4-oxo-4H-1-benzopyran-2-carboxamide, N-[4-[(2-oxazolidon-3-yl)methyl]phenyl]-4-oxo-4H-1-benzopyran-2-carboxamide, N-[4-[(2,6-dioxo-1-piperidinyl)methyl]phenyl]-4-oxo-4H-1-benzopyran-2-carboxamide, 5-hydroxy-N-[4-[2,4-dioxooxazolidin-5-yl)methyl]phenyl]-4-oxo-4H-1-benzopyran-2-carboxamide, 5-hydroxy-N-methyl-N-[4-[(4-morpholinyl)methyl]phenyl]-4-oxo-4H-1-benzopyran-2-carboxamide, or 4-oxo-N-[4-[(4-oxo-1-piperidinyl)methyl]phenyl]-4H-1-benzopyran-2-carboxamide, or a salt thereof.

As the salts of the compounds of the present invention, pharmaceutically acceptable salts are preferred, including, for example, salts with inorganic bases, salts with organic bases, salts with inorganic acids, salts with organic acids, and salts with basic or acidic amino acids, and the like. The preferred salts with inorganic bases are exemplified by alkali metal salts, e.g., sodium salts, potassium salts, etc.; alkaline earth metal salts, e.g., calcium salts, magnesium salts, etc.; as well as aluminum salts, ammonium salts, and the like. The preferred salts with organic bases are exemplified by salts of trimethylamine, triethylamine, pyridine, picoline, ethanolamine, diethanolamine, dicyclohexylamine, N,N'-dibenzylethylenediamine, and the like. The preferred salts with inorganic acids are exemplified by those of hydrochloric acid, hydrobromic acid, nitric acid, sulfuric acid, phosphoric acid, and the like. The preferred salts with organic acids are exemplified by those of formic acid, acetic acid, trifluoroacetic acid, fumaric acid, oxalic acid, tartaric acid, maleic acid, citric acid, succinic acid, malic acid, methanesulfonic acid, benzensulfonic acid, p-toluene sulfonic acid, and the like. The preferred salts with basic amino acids are exemplified by those of arginine, lysine, ornithine, and the like. The salts with acidic amino acids are those of aspartic acid, glutamic acid, and the like.

The present invention further provides a process for producing the compound described in the above Formula (I), or a salt thereof.

The compound represented by the Formula (I) or a salt thereof [sometimes referred to as Compounds (I)], is produced according to, for example, Method A described below. A salt of the compounds represented by the Formula (II) and Formula (III) includes the same salt as the salt of the compound represented by the Formula (I).

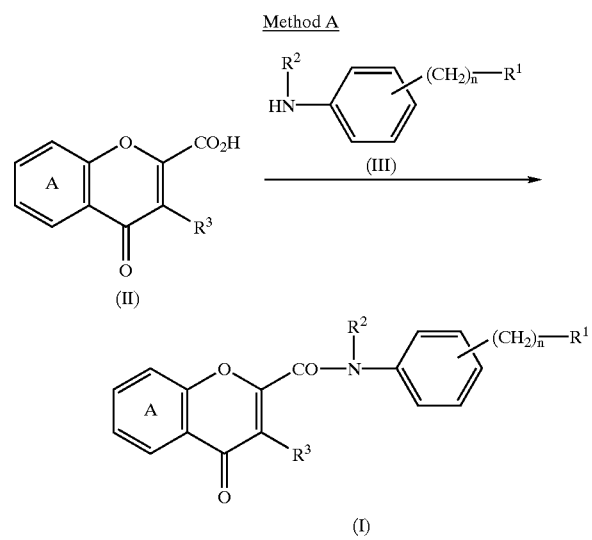

Method A wherein each symbol has the same meaning as mentioned above. Compounds (I) can be prepared by reacting Compounds (II) (equivalent to the compound of the Formula (II) or a salt thereof) with Compounds (III) (equivalent to the compound of the Formula (III) or a salt thereof). The condensation reaction of Compounds (II) with Compounds (III) can be conducted by the general method of peptide synthesis.

Publicly known methods for the peptide synthesis, for example, are described in 1)–3) below.

1) M. Bodansky & M. A. Ondetti: Peptide Synthesis, Interscience Publishers, New York (1966)

2) F. M. Finn & K. Hofmann: The Proteins, Vol.2, (edited by H. Nenrath, R. L. Hill), published by Academic press Inc. New York (1976), 3) Nobuo Izumiya, et al.: *Peptide Gosei-no-Kiso to Jikken* (Basics and experiments of peptide synthesis), published by Maruzen Co. (1985)

The methods used include, for example, the acyl azide method, acyl chloride method, acid anhydride method, mixed acid anhydride method, DCC method, activated ester method, the method using Woodward's reagent K, carbonylimidazole method, oxidation-reduction method, DCC/HONB method and the method using diethylcyanophosphonate (DEPC). The condensation reaction can be carried out in solvents.

As solvents (hydrous/anhydrous), for example, dimethylformamide, dimethylsulfoxide, pyridine, chloroform, dichloromethane, tetrahydrofuran, dioxane, acetonitrile, and appropriate mixtures of these solvents are used. The reaction temperature is usually selected in the range of approximately −20° C. to 50° C., more preferably −10° C. to 30° C. The reaction time is usually about 1 to 100 hours, more preferably 2 to 40 hours approximately.

Publicly known methods (e.g. oxidation reaction, reduction reaction, acylation reaction, ester reaction, amide reaction, and the like) are applied to produce different Compounds (I) from the Compounds (I) obtained by the methods above.

Compounds (I) thus obtained can be isolated and purified by the publicly known methods for separation and purification, for example, concentration, reduced pressure concentration, solvent extraction, crystallization, recrystallization, solvent exchange and chromatography.

The above-mentioned starting Compounds (II) can be produced according to publicly known methods such as the method described in Progress in Medicinal Chemistry, vol. 9, 65, 1973, Liebigs Annalen der Chemie, 1552, 1973 and Journal of Chemical Society Perkin Transactions I, 2597, 1987. More specifically, for example, they can be prepared by Method B or Method C described next.

Method B

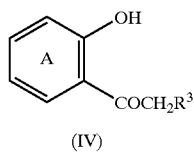
(IV)

i) $(CO_2R^8)_2$
ii) acid

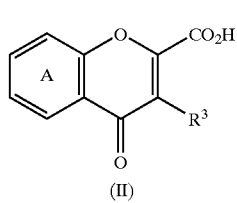
(II)

wherein $R^8$ represents $C_{1-10}$ alkyl group and other symbols have the same meaning as mentioned above.

The same group as $R^1$–$R^3$ exemplified in the above is used to represent the $C_{1-10}$ alkyl group represented by $R^8$.

Further, the compound shown in the formula (II) or its salt is exemplified by 5,6-methylenedioxy-4-oxo-4H-1-benzopyran-2-carboxylic acid, 5,6-dihydroxy-4-oxo-4H-1-benzopyran-2-carboxylic acid, or 5-hydroxy-7-methyl-4-oxo-4H-1-benzopyran-2-carboxylic acid, or a salt thereof, and the like. 5,6-Methylenedioxy-4-oxo-4H-1-benzopyran-2-carboxylic acid, 5,6-dihydroxy-4-oxo-4H-1-benzopyran-2-carboxylic acid and 5-hydroxy-7-methyl-4-oxo-4H-1-benzopyran-2-carboxylic acid or a salt thereof are new compounds.

In Method B, to produce Compounds (II), first, the compound represented by formula (IV) or its salt (hereinafter referred to as Compound VI) is reacted with oxalic acid ester (the reaction of the 1$^{st}$ step), then, treated with an acid (the reaction of the 2$^{nd}$ step).

The reaction of the 1$^{st}$ step is conducted in solvents in the presence of a base. Examples of suitable solvents are aromatic hydrocarbons such as benzene, toluene, xylene, etc.; a halogenated hydrocarbons such as chloroform, dichloromethane, 1,2-dichloroethane, 1,1,2,2-tetrachloroethane, etc.; ethers such as diethylether, tetrahydrofuran, dioxane, etc.; alcohols such as methanol, ethanol, propanol, 2-methoxyethanol, etc.; N,N-dimethylformamide; dimethylsulfoxide; and appropriate mixtures of these solvents. Examples of suitable bases are sodium alkoxides such as sodium methoxide, sodium ethoxide, etc.; potassium alkoxides such as potassium methoxide, potassium, tert-butoxide, etc.; sodium hydride; potassium hydride; sodium hydroxide; potassium hydroxide. The molar ratio of the amount of oxalic acid ester used to Compounds (IV) is about 1–3 mol to 1 mol. The amount of the base used to Compounds (IV) is about 1 to 10 mol per 1 mol, preferably 2 to 5 mol per 1 mol. The reaction temperature is from about −20 to 150° C., more preferably from about 0 to 120° C. The reaction time is from about 0.5 to 10 hours.

Using the compound obtained from the 1$^{st}$ step, Compound (II) is manufactured according to the 2$^{nd}$ step of reaction. The 2$^{nd}$ step is conducted by heating with inorganic acids such as hydrochloric acid, sulfuric acid, etc. in solvents. Examples of suitable solvents are ethers such as diethylether, tetrahydrofuran, dioxane, etc.; alcohols such as methanol, ethanol, propanol, 2-methoxyethanol, etc.; acetic acid; N,N-dimethyl formamide; dimethyl sulfoxide; acetonitrile; 2-butanone; water; and mixtures of these solvents. An excess amount of inorganic acid is normally used. The reaction temperature is from about 20 to 180° C. The reaction time is from about 0.5 to 30 hours.

The compounds (II) thus obtained can be isolated and purified by publicly known methods for separation and purification, for example, concentration, reduced pressure concentration, solvent extraction, crystallization, recrystallization, solvent exchange and chromatography.

Method C

(V)

i) $R^8O_2CC\equiv CCO_2R^8$
ii) acid

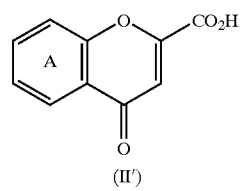
(II')

wherein $R^8$ has the same meaning as mentioned above.

In method C, the compound represented by Formula (V) or its salt (referred to as Compounds (V)) is reacted with acetylene dicarboxylic acid ester (the 1$^{st}$ step of reaction), then, treated with acids (the 2$^{nd}$ step of the reaction) in order to manufacture Compounds (II') (equivalent to Compounds represented by formula (II') or its salt thereof).

The 1$^{st}$ step of the reaction is conducted in solvents in the presence of a base. Examples of suitable solvents are aromatic hydrocarbons such as benzene, toluene, xylene, etc.; halogenated hydrocarbons such as chloroform, dichloromethane, 1,2-dichloroethane, 1,1,2,2-tetrachloroethane, etc.; ethers such as diethyl ether, tetrahydrofuran, dioxane, etc.; alcohols such as methanol, ethanol, propanol, 2-methoxyethanol, etc.; N,N-dimethylformamide; dimethylsulfoxide; and appropriate mixtures of these solvents. Examples of suitable bases are phase transfer catalysts such as tetrabutylammonium fluoride (TBAF); sodium alkoxides such as sodium methoxide, sodium ethoxide, etc.; potassium alkoxides such as potassium methoxide, potassium tert-butoxide, etc.; sodium hydride; potassium hydride; sodium hydroxide; potassium hydroxide. The molar ratio of the acetylene dicarboxylic acid ester used to Compounds (V) is about 1 to 3 mol per 1 mol. The molar ratio of the base used to Compounds (V) is about 0.1 to 10 mol per 1 mol, preferably 0.4 to 5 mol per 1 mol. The reaction temperature is about −20 to 150° C., preferably, about 0 to 120° C. The reaction time is about 0.5 to 10 hours.

Using the compound obtained from the $1^{st}$ step, Compound II is manufactured according to the $2^{nd}$ step of reaction. The $2^{nd}$ step is conducted by heating with inorganic acids such as hydrochloric acid, sulfuric acid, etc. in solvents. Examples of suitable solvents are ethers such as diethylether, tetrahydrofuran, dioxane, etc.; alcohols such as methanol, ethanol, propanol, 2-methoxyethanol, etc.; acetic acid; N,N-dimethylformamide; dimethylsulfoxide; acetonitrile; 2-butanone; water; and mixtures of these solvents. An excess amount of inorganic acid is normally used. The reaction temperature is about 20° C. to 180° C. The reaction time is about 0.5 to 30 hours.

The compounds (II') thus obtained can be isolated and purified by publicly known methods for separation and purification, for example, concentration, reduced pressure concentration, solvent extraction, crystallization, recrystallization, solvent exchange and chromatography.

The prodrugs of Compounds (I) of the invention mean compounds convertible into Compounds (I) under the action of enzymes or gastric acid under physiological conditions in a living body, that is, compounds which are enzymatically oxidized, reduced or hydrolyzed to give Compounds (I), or compounds which are hydrolyzed with gastric acid or the like to give Compounds (I).

The prodrugs of Compounds (I) include: the compound in which the amino group of Compounds (I) is acylated, alkylated or phosphorylated (e.g., the compound in which the amino acid group of Compounds (I) is eicosanoylated, alanylated, pentylaminocarbonylated, (5-methyl-2-oxo-1,3-dioxolene-4-yl)methoxycarbonylated, tetrahydrofuranylated, pyrrolidylmethylated, pivaloyloxymethylated, tert-butylated etc.); the compound in which the hydroxyl group of Compounds (I) is acylated, alkylated, phosphorylated or borated (e.g., the compound in which the hydroxyl group of Compounds (I) is acetylated, palmitoylated, propanoylated, pivaloylated, succinylated, fumarylated, alanylated, dimethylaminomethylcarbonylated, etc.); the compound in which the carboxyl group of Compounds (I) is esterified and/or amidated (e.g., the compound in which the carboxyl group of Compounds (I) is ethylesterified, phenylesterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolene-4-yl)methyl esterified, cyclohexyloxycarbonylethyl esterified, methylamidated, etc.), and the like. These compounds may be prepared from Compounds (I) in a per se known method.

Alternatively, the prodrug of Compounds (I) may be those which can be converted into Compounds (I) under physiological conditions as described in "Development of Drugs", vol. 7, Molecular Design, pp. 163–198 (1990), Hirokawa Publishing Company.

Moreover, Compounds (I) may be hydrates of those mentioned.

Compounds (I) of the present invention, since they exhibit a potent alkaline phosphatase-inducing activity, have a potent osteogenesis promoting effect, chondrogenesis promoting effect, cartilage destruction suppressing effect, and cartilage cell differentiation inducing promoting effect, and in addition they are superior in clinically useful characteristics such as stability, absorption, (particularly, oral absorption), bioavailability, and the like. In addition, their toxicity is low. Accordingly, they can be used safely in mammals (e.g., human, rat, mouse, dog, rabbit, cat, cattle, horse, pig, etc.).

The osteogenesis promoting agents, preventive agents for bone diseases, preventive agents for bone fractures and preventive agents for cartilage diseases which contain Compounds (I) of the present invention having such effects, can be used as preventive or therapeutic agents for bone diseases and cartilage diseases such as fracture, refracture, bone defect, osteomalacia, Paget's disease of bone, sclerosing myelitis, chronic rheumatoid arthritis, osteoarthritis (e.g., osteoarthritis of the knee), osteoarthritis involving cartilage, and the like in the orthopaedic region, as well as used as osseous tissue restoration agents after surgery for multiple myeloma, lung cancer, breast cancer, and the like. Moreover, in the dental field, they are expected to apply to treatment of periodontal diseases, restoration of periodontal tissue defects in periodontal diseases, stabilization of artificial tooth roots, residual ridge formation and repair of cleft palate.

Compounds (I) of the present invention, when used as preventive or therapeutic agents for osteoporosis, fracture, cartilage defect, etc., may be administered orally at a daily dose of about 1 mg to about 500 mg, preferably about 10 mg to about 100 mg, as active ingredient (Compound (I) of the present invention) for an adult (body weight 50 kg) in 1 to 3 divided doses, while the dose varies depending on the state or weight of a patient, the administration manner and the like.

In parenteral administration, they may be administered at a daily dose of about 1 mg to about 300 mg, as active ingredients (Compound (I) of the present invention) for an adult (body weight 50 kg) in 1 to 3 divided doses.

Compounds (I) of the present invention can be used in combination with other bone resorption suppressing agents or osteogenesis promoting agents. The agents used in combination are exemplified by vitamins $D_3$ (e.g., 1-hydroxyvitamin $D_3$, 1, 25-dihydroxyvitamin $D_3$, flocalcitriol, secalciferol, etc.), calcitonins (e.g., eel calcitonin, salmon calcitonin, porcine calcitonins, avicatonin, etc.), bisphosphonic acids (e.g., etidronate, simadronate, alendronate, tiludronate, risedronate, clodronate, etc.), sex hormone related compounds (e.g., tibolone, estradiol, osaterone, raloxifene, droloxifene, ormeloxifene, tamoxifene, mifepristone, etc.), ipriflavone, vitamins $K_2$ (e.g., menatetrenone), sodium fluoride, parathyroid hormones (PTH)(1–34), PTH (1–84), PTH (1–36), etc.), and the like.

Compounds (I) of the present invention can be used in combination with other bone resorption suppressing agents or osteogenesis promoting agents. The agents used in combination are exemplified by vitamins $D_3$ (e.g., 1α-hydroxyvitamin $D_3$, 1α,2,5-dihydroxyvitamin $D_3$, flocalcitriol, secalciferol, etc.), calcitonins (e.g., eel calcitonin, salmon calcitonin, porcine calcitonins, avicatonin, etc.), bisphosphonic acids (e.g., etidronate, simadronate, alendronate, tiludronate, risedronate, clodronate, etc.), sex hormone related compounds (e.g., tibolone, estradiol, osaterone, raloxifene, droloxifene, ormeloxifene, tamoxifene, mifepristone, etc.), ipriflavone, vitamins $K_2$ (e.g., menatetrenone), sodium fluoride, parathyroid hormones (PTH)(1–34), PTH (1–84), PTH (1–36), etc.), and the like.

As the pharmaceutically acceptable carriers, a variety of conventional organic or inorganic carrier materials usually added to pharmaceutical preparations can be used, including excipients, lubricants, binders, disintegrators, etc., in solid preparations; solvents, dissolution aids, suspending agents, isotonization agents, buffering agents, soothing agents, etc., in liquid preparations. If required, pharmaceutical additives such as preservatives, antioxidants, stabilizers, coloring agents, sweeteners, and the like may be added. The preferred excipients include, for example, lactose, refined sugar, D-mannitol, starch, crystalline cellulose, light silicic anhydride, and the like. The preferred lubricants include, for example, magnesium stearate, calcium stearate, talc, colloidal silica, and the like. The preferred binders include, for example, crystalline cellulose, α-starch, refined sugar, D-mannitol, dextrin, hydroxypropyl cellulose, hydroxypropyl methyl cellulose, polyvinylpyrrolidone, and the like. The preferred disintegrators include, for example, starch, carboxymethyl cellulose, carboxymethyl cellulose calcium, croscarmellos sodium, carboxymethyl starch sodium, low-substituted hydroxypropyl cellulose, and the like. The preferred solvents include, for example, water for injection, alcohol, propylene glycol, macrogol, sesame oil, corn oil, and the like.

The preferred dissolution aids include, for example, polyethylene glycol, propylene glycol, D-mannitol, benzyl benzoate, ethanol, trisaminomethane, cholesterol, triethanolamine, sodium carbonate, sodium citrate, and the like. The preferred suspending agents include, for example, surface activators such as stearyl triethanolamine, sodium lauryl-sulfate, laurylaminopropionic acid, lecithin, benzalkonium chloride, glycerin monostearate, etc.; and hydrophilic high molecular materials such as polyvinyl alcohol, polyvinylpyrrolidone, carboxymethylcellulose sodium, methylcellulose, hydroxymethyl cellulose, hydroxyethyl cellulose, hydroxypropyl cellulose, etc. The preferred isotonization agents include, for example, sodium chloride, glycerin, D-Mannitol, and the like. The preferred buffering agents include, for example, buffer solutions containing phosphate, acetate, carbonate, citrate, and the like. The preferred soothing agents include, for example, benzyl alcohol, etc. The preferred preservatives include, for example, paraoxybenzoic acid esters, chlorobutanol, benzyl alcohol, phenethyl alcohol, dehydroacetic acid, sorbic acid, and the like. The preferred anti-oxidants include, for example, sulfites, ascorbic acid, and the like.

Moreover, if required, the oral preparation may be coated in a per se conventional manner in order to mask its taste or give enteric coating preparations or sustained-release preparations. The coating agents include, for example, hydroxypropyl methyl cellulose, ethyl cellulose, hydroxymethy cellulose, hydroxypropyl cellulose, polyoxyethylene glycol, Tween 80, Pluronic F68, cellulose acetate phthalate, hydroxypropyl methyl cellulose phthalate, hydroxymethyl cellulose acetate succinate, Eudragit (methacrylic acid/acrylic acid copolymer; Rohm Pharma GmbH, Germany), and the like.

In addition to the formulations prepared according to the above-mentioned conventional pharmaceutical technique, Compounds (I) of the present invention may also be formulated into sustained-release preparations according to a technique for sustained-release formulation. A method for preparing sustained-release preparations, as described in JP-A 9-263545/1997, comprises dispersing Compound (I) into an aliphatic polyester such as lactic acid/glycolic acid copolymer according to the in-water drying method, phase separation method, spray drying method, and the like. The sustained-release preparations prepared by these methods can be applied locally as a suspension of microcapsules or microspheres.

Compounds (I) of the invention are preferably added to a pharmaceutical composition together with polyethylene glycol, as described in JP-A 10-338646/1998.

Moreover, when administered directly into the cavitas articularis as a local medicament, Compound (I) may be dispersed into a hyaluronic acid preparation for injection (for example, Kaken Pharm. Co., Ltd.; ARTZ injection) as a dispersing agent. Hyaluronic acid used in a dispersing medium may be used in a form of non-toxic salts, for example, alkali metal salts, e.g., salts with sodium, potassium, etc., or alkaline earth metal salts, e.g., salts with magnesium, calcium, etc., and particularly, the sodium salt is preferably used. The average molecular weight of hyaluronic acid or its non-toxic salts to be used is approximately 200,000–5,000,000, preferably, approximately 500,000–3,000,000, more preferably, approximately 700,000–2,500,000 (viscometrically).

The final concentration of hyaluronic acid or its sodium salt in the dispersing medium is preferably fixed at less than 1% (w/v) giving an appropriate viscosity to facilitate various operations or administration, particularly less than 0.02–1%, more preferably about 0.1–1% (w/v).

Into the above-mentioned dispersing medium, it is possible to add a pH regulator, local anesthetic, antibiotic, dissolution aid, isotonization agent, adsorption preventing agent, glycosaminoglycan, polysaccharide, and the like in a per se known manner. The preferred additives are, for example, mannitol, sorbitol, sodium chloride, glycine, ammonium acetate, or substantially pharmaceutically inactive water-soluble proteins injectable into the body. The glycosaminoglycan includes, for example, hyaluronic acid, chondroitin, chondroitin sulfate A, chondroitin sulfate C, dermatan sulfate, heparin, heparan sulfate, keratin sulfate, and the like. The polysaccharides include acidic ones such as alginic acid.

The above-mentioned water-soluble proteins include those that are soluble in water, physiological saline, or buffer solution, for example, human serum albumin, human serum globulin, collagen, gelatin, and the like. When a water-soluble protein is contained in a dispersing medium, the content of the protein is preferably 0.05–50 mg per dosage, more preferably 0.5–20 mg, particularly 0.75–10 mg.

The above-mentioned pH regulator includes, for example, glycine, ammonium acetate, citric acid, hydrochloric acid, sodium hydroxide, and the like. The above-mentioned local anesthetic includes, for example, chlorobutanol, lidocaine hydrochloride, and the like. The above-mentioned antibiotics include, for example, gentamicin, etc. The above-mentioned dissolution aids includes, for example, glycerin, polyethylene glycol 400, and the like. The above-mentioned isotonization agents include, for example, mannitol, sorbitol, sodium chloride, and the like. The above-mentioned adsorption preventing agents include, for example, polyoxyethylene sorbitan mono-oleate, etc.

The pharmaceutical preparation may also contain phosphoric acid or its salts (for example, sodium phosphate, potassium phosphate, etc.). When the preparation for injection contains phosphoric acid or its salts, the concentration of sodium phosphate or potassium phosphate is about 0.1 mM to 500 mM, preferably about 1 mM to 100 mM.

EXAMPLES

The invention will be explained in more detail based on the following Reference Examples, Examples, and Test Example, but the invention is not restricted by these examples.

Reference Example

Preparation of N-methoxy-N-methyl-2-methoxymethoxy-5,6-methylenedioxybenzamide A mixture of 2-methoxymethoxy-5,6-methylenedioxy benzoic acid (9.05 g), N,O-dimethylhydroxylamine hydrochloride (5.13 g), 1-ethyl-3-(3-dimethylaminopropyl) carbodiimide hydrochloride (8.53 g), triethylamine (7.5 ml), and 1-hydroxybenzotriazole (HOBt) (5.95 g) in N,N-dimethyl formamide (DMF) (100 ml) was stirred at room temperature for 12 hours. The mixture was diluted with a mixture of ethyl acetate (100 ml) and water (100 ml). The organic layer was washed with an aqueous solution of saturated sodium hydrogencarbonate, water, 1N hydrochloric acid, water and saturated brine, successively. The solution was dried ($MgSO_4$). Then, the solvent was evaporated. The residue was purified by silica gel column chromatography and gave the colorless oily substance of the title compound (4.95 g, 46%). $^1$H NMR($CDCl_3$) δ:3.39(3H, s), 3.47(3H, s), 3.58(3H, s), 5.11(2H, s), 5.98(2H, s), 6.60(1H, d, J=8.6 Hz), 6.74(1H, d, J=8.6 Hz).

Preparation of 2'-methoxymethoxy-5',6'-methylenedioxy acetophenone

A solution of N-methoxy-N-methyl-2-methoxymethoxy-5,6-methylenedioxybenzamide (4.95 g) in ether (100 ml) was cooled down to −30° C. Then, methylmagnesium bromide (3.0M ether solution, 3 ml) was added to the mixture and stirred for an hour. And furthermore, methyl magnesium bromide (3.0M ether solution, 3 ml) was added to the mixture and stirred for an additional hour. An aqueous solution of oxalic acid was added to the mixture. The mixture was extracted with ethyl acetate. The extract was washed with an aqueous solution of saturated sodium hydrogencarbonate, water, 1N hydrochloric acid, water and saturated brine, successively. The solution was dried ($MgSO_4$). Then, the solvent was evaporated. The residue was purified by silica gel column chromatography and gave the colorless oily substance of the title compound (2.1 g, 51%). $^1$H NMR($CDCl_3$) δ:3.39(3H, s), 3.47(3H, s), 3.58(3H, s), 5.11(2H, s), 5.98(2H, s), 6.60(1H, d, J=8.6 Hz), 6.74(1H, d, J=8.6 Hz).

Preparation of 5,6-methylenedioxy-4-oxo-4H-1-benzopyran-2-carboxylic acid

To a solution of sodium (0.65 g) in ethanol (30 ml) was added 2'-methoxymethoxy-5',6'-methylenedioxyacetophenone (1.4 g) and ethyl oxalate (1.64 g). The mixture was refluxed under heating for 2 hours. The reaction solution was cooled down and the precipitated salts were collected by filtration. The precipitants were dissolved in 2N hydrochloric acid and extracted with ethyl acetate. The extract was washed with water and saturated brine. The solution was dried ($MgSO_4$). Then, the solvent was evaporated. The oily substance obtained was dissolved in acetic acid (6 ml) and hydrochloric acid (6 ml) and refluxed under heating for 2 hours. The mixture was cooled down. The precipitated crystals were collected by filtration and the title compound was obtained (1.36 g, 72%). $^1$H NMR($CDCl_3$) δ:6.26(2H, s), 6.73(1H, s), 7.16(1H, d, J=8.8 Hz), 7.41(1H, d, J=8.8 Hz).

Preparation of 5,6-dihydroxy-4-oxo-4H-1-benzopyran-2-carboxylic acid

To a solution of 5,6-methylenedioxy-4-oxo-4H-1-benzopyran-2-carboxylic acid (0.475 g) in dichloromethane (20 ml) was added aluminum chloride (0.48 g). The mixed solution was stirred at room temperature for 2 hours. The reaction solution was poured into 2N hydrochloric acid and extracted with chloroform. The extract was washed with water and saturated brine. The solution was dried ($MgSO_4$). Then, the solvent was evaporated and the title compound was obtained (0.169 g, 38%). $^1$H NMR(DMSO-$d_6$) δ:6.85 (1H, s), 7.06(1H, d, J=9.2 Hz), 7.33(1H, d, J=9.2 Hz), 9.58 (1H,s), 12.09(1H,s)

Preparation of 5-methoxy-7-methyl-4-oxo-4H-1-benzopyran-2-carboxylic acid

To a solution of sodium (0.41 g) and ethanol (30 ml) was added 2'-hydroxy-6'-methoxy-4'-methylacetophenone (1.08 g) and ethyl oxalate (0.96 g). The reaction solution was cooled down and the precipitated salts were collected by filtration. The precipitants were dissolved in 2N hydrochloric acid and extracted with ethyl acetate. The extract was washed with water and saturated brine. The solution was dried ($MgSO_4$). Then, the solvent was evaporated. The oily substance obtained was dissolved in acetic acid (3 ml) and hydrochloric acid (3 ml) and refluxed under heating for 2 hours. The mixture was cooled down. The precipitated crystals were collected by filtration and the title compound was obtained (0.78 g, 55%). $^1$H NMR(DMSO-$d_6$) δ:2.69 (3H, s), 3.89(3H,s), 6.72(1H,s), 6.86(1H, d, J=2.2 Hz), 7.01(1H, d, J=2.2 Hz).

Preparation of 5-hydroxy-7-methyl-4-oxo-4H-1-benzopyran-2-carboxylic acid

To the solution of 5-methoxy-7-methyl-4-oxo-4H-1-benzopyran-2-carboxylic acid (0.555 g) in dichloromethane (20 ml) was added aluminum chloride (0.63 g). The mixture was stirred at room temperature for 2 hours. The reaction solution was poured into 2N hydrochloric acid and extracted with chloroform. The extract was washed with water and saturated brine. The solution was dried ($MgSO_4$). Then, the solvent was evaporated and the title compound was obtained (0.405 g, 78%).

$^1$H NMR(DMSO-$d_6$) δ:2.66(3H, s), 6.68(1H, S), 6.69(1H, d, J=2.2 Hz), 6.738(1H, d, J=2.2 Hz).

Preparation of 5-butyryloxy-4-oxo-4H-1-benzopyran-2-carboxylic acid a) 5-butyryloxy-4-oxo-4H-1-benzopyran-2-carboxylic acid benzyl ester To a mixture of 5-hydroxy-4-oxo-4H-1-benzopyran-2-carboxylic acid benzyl ester (1.00 g) and 4-(N,N-dimethylamino)pyridine (0.042 g) in pyridine solution (10 ml) was added butyrylchloride (1.1 ml) at room temperature and stirred for 14 hours. Then, the reaction solution was poured into water and extracted with ethyl acetate. The organic layer was washed with diluted hydrochloric acid, an aqueous solution of saturated sodium hydrogencarbonate and ammonium chloride, successively. The solution was dried (MgSO$_4$) and evaporated under reduced pressure. The residue was purified by silica gel column chromatography. The title compound was obtained as colorless crystals 1.10 g(89%). mp 103–105° C.

b) 5-butyryloxy-4-oxo-4H-1-benzopyran-2-carboxylic acid

5-Butyryloxy-4-oxo-4H-1-benzopyran-2-carboxylic acid benzyl ester (1.000000 g) and palladium-carbon (5%, 0.20 g) in ethyl acetate (100 ml) were stirred under a hydrogen atmosphere for 30 minutes. Insoluble material was filtered off. The filtered solution was concentrated under reduced pressure. The title compound was obtained as colorless crystals 0.72 g (95%). mp 218–220° C.

Preparation of 5-isobutyryloxy-4-oxo-4H-1-benzopyran-2-carboxylic acid a) 5-isobutyryloxy-4-oxo-4H-1-benzopyran-2-carboxylic acid benzyl ester To a solution of 5-hydroxy-4-oxo-4H-1-benzopyran-2-carboxylic acid benzyl ester (1.00 g) and 4-(N,N-dimethylamino)pyridine(0.042 g)in pyridine solution (10 ml) was added isobutyrylchloride(1.1 ml) at room temperature. The mixture was stirred for 14 hours. The reaction solution was poured into water and extracted with ethyl acetate. The organic layer was washed with diluted hydrochloric acid, an aqueous solution of sodium hydrogencarbonate and ammonium chloride, successively. The solution was dried (MgSO$_4$) and evaporated under reduced pressure. The residue was purified by silica gel column chromatography. The title compound was obtained as colorless crystals 1.20 g(97%). mp 90–92° C.

b) 5-isobutyloxy-4-oxo-4H-1-benzopyran-2-carboxylic acid 5-isobutyloxy-4-oxo-4H-1-benzopyran-2-carboxylic acid benzyl ester (1.00 g) and palladium-carbon (5%, 0.20 g) in ethyl acetate (100 ml) were stirred under a hydrogen atmosphere for 30 minutes. Insoluble material was filtered off. The filtered solution was concentrated under reduced pressure. The title compound was obtained as colorless crystals 0.64 g (85%). mp 206–208° C.

Preparation of 5-diethylcarbamoyloxy-4-oxo-4H-1-benzopyran-2-carboxylic acid a) 5-diethylcarbamoyloxy-4-oxo-4H-benzopyran-2-carboxylic acid benzyl ester To a solution of 5-hydroxy-4-oxo-4H-1-benzopyran-2-carboxylic acid benzyl ester (1.00 g), 4-(N,N-dimethylamino)pyridine (0.082 g) and triethylamine (0.94 ml) in THF solution (30 ml) was added diethylcarbamoylchloride (0.86 ml) under ice cooling. The solution was stirred at 45° C. for 24 hours. The solution was poured into water and extracted with ethyl acetate. The organic layer was washed with diluted hydrochloric acid, an aqueous solution of sodium hydrogencarbonate and an aqueous solution of ammonium chloride, successively. The solution was dried (MgSO$_4$) and evaporated under reduced pressure. The title compound was obtained as colorless crystals 1.25 g(94%). mp 104–106° C.

b) 5-diethylcarbamoyloxy-4-oxo-4H-1-benzopyran-2-carboxylic acid 5-diethylcarbamoyloxy-4-oxo-4H-1-benzopyran-2-carboxylic acid benzyl ester (1.13 g) and palladium-carbon (5%, 0.20 g) in ethyl acetate (100 ml) were stirred under a hydrogen atmosphere for 30 minutes. Insoluble material was filtered off. The filtered solution was concentrated under reduced pressure. The title compound was obtained as colorless crystals 0.82 g (94%). mp 104–106° C.

Example 1

Preparation of N-[4-[(2,4-dioxo-1,3-thiazolidin-5-yl)methyl]phenyl]-4-oxo-4H-1-benzopyran-2-carboxamide To a solution of 4-oxo-4H-1-benzopyran-2-carboxylic acid (0.191 g), 5-(4-aminobenzyl)-2,4-dioxothiazolidine (0.223 g) and 1-ethyl-3-(3-dimethylaminopropyl)carbodiimide hydrochloride (0.288 g) in DMF (10 ml) was added 1-hydroxybenzotriazole (HOBt) (0.162 g) and stirred at room temperature for 14 hours. The reaction solution was poured into water and extracted with chloroform. The extract was washed with an aqueous solution of sodium hydrogencarbonate, an aqueous solution of ammonium chloride and saturated brine. The solution was dried (MgSO$_4$). Then, the solvent was evaporated. The residue was purified by silica gel column chromatography. The obtained crystals were washed with ethyl acetate to afford the title compound 0.117 g(30%). mp 284–287° C.

Example 2

Preparation of N-[4-[(2,4-dioxo-1,3-oxazolidin-5-yl)methyl]phenyl]-4-oxo-4H-1-benzopyran-2-carboxamide To a solution of 4-oxo-4H-1-benzopyran-2-carboxylic acid (0.270 g), 5-(4-aminobenzyl)-2,4-dioxooxazolidine (0.295 g) and 1-ethyl-(3-dimethylaminopropyl)carbodiimide hydrochloride (0.550 g) in DMF(20 ml) was added 1-hydroxybenzotriazole (HOBt)(0.290 g), and the mixture was stirred at room temperature for 14 hours. The reaction solution was poured into a mixture solution of ethyl acetate and water. The ethyl acetate layer was washed with an aqueous solution of diluted hydrochloric acid, an aqueous solution of sodium hydrogencarbonate and saturated brine, successively. The solution was dried (MgSO$_4$) and evaporated. The obtained crystals were washed with isopropyl ether to afford the title compound 0.372 g(70%). mp 265–267° C.

Example 3

Preparation of 4-oxo-N-[4-[(2-oxo-1,3-oxazolidin-3-yl)methyl]phenyl]-4H-1-benzopyran-2-carboxamide To a solution of 4-oxo-4H-1-benzopyran-2-carboxylic acid (0.371 g), 3-(4-aminobenzyl)-2-oxazolidine (0.375 g) and 1-ethyl-3-(3-dimethylaminopropyl)carbodiimide hydrochloride (0.411 g) in DMF(6 ml) was added 1-hydroxybenzotriazole (HOBt)(0.288 g) at room temperature and stirred for 14 hours. The reaction solution was poured into water and extracted with a mixture solution of ethyl acetate and THF. The extract was washed with water, an aqueous solution of sodium hydrogencarbonate and saturated brine. The solution was dried (MgSO$_4$) and evaporated. The obtained crystals were recrystallized from THF-ethyl acetate to afford the title compound 0.591 g(83%). mp 237–238° C.

Example 4

Preparation of N-[4-[(2,6-dioxo-1-piperidinyl)methyl]phenyl]-4-oxo-4H-1-benzopyran-2-carboxamide To a solution of 4-oxo-4H-1-benzopyran-2-carboxylic acid (0.23 g), 1-(4-aminobenzyl)glutarimide hydrochloride (0.300 g) and 1-ethyl-3-(3-dimethylaminopropyl)carbodiimide hydrochloride (0.464 g) in DMF (20 ml) was added 1-hydroxybenzotriazole (HOBt) (0.245 g) and stirred at room temperature for 14 hours. The reaction solution was poured into water and extracted with a mixture solution of ethyl acetate and THF. The extract was washed with diluted hydrochloric acid, an aqueous solution of sodium hydrogencarbonate and saturated brine. The solution was dried (MgSO$_4$) and evaporated. The obtained crystals were washed with isopropyl ether to afford the title compound 0.4 g(87%). mp 190–192° C.

Example 5

Preparation of N-[4-[(4-morpholinyl)methyl]phenyl]-4-oxo-4H-1-benzopyran-2-carboxamide To a solution of 4-oxo-4H-1-benzopyran-2-carboxylic acid (0.4 g), 4-(4-aminobenzyl)morpholine (0.385 g) and 1-ethyl-3-(3-dimethylaminopropyl)carbodiimide hydrochloride (0.805 g) in DMF (15 ml) was added 1-hydroxybenzotriazole (HOBt)(0.426 g), and the mixture was stirred at room temperature for 14 hours. The reaction solution was added to a mixture solution of water and ethyl acetate and extracted with ethyl acetate. The extract was washed with an aqueous solution of sodium hydrogencarbonate, an aqueous solution of ammonium chloride and saturated brine. The solution was dried (MgSO$_4$) and evaporated. The obtained crystals were washed with isopropyl ether/hexane to afford the title compound 0.65 g(89%). mp 201–203° C.

Example 6

Preparation of 4-oxo-N-[4-[(4-thiomorpholinyl)methyl]phenyl]-4H-1-benzopyran-2-carboxamide To a solution of 4-oxo-4H-1-benzopyran-2-carboxylic acid (0.296 g), 1-(4-aminobenzyl)thiomorpholine (0.36 g) and 1-ethyl-3-(3-dimethylaminopropyl)carbodiimide hydrochloride (0.366 g) in DMF (10 ml) was added 1-hydroxybenzotriazole(HOBt) (0.262 g), and the mixture was stirred at room temperature for 14 hours. The reaction solution was poured into water and extracted with a mixture solution of ethyl acetate and THF. The extract was washed with an aqueous solution of sodium hydrogencarbonate, an aqueous solution of ammonium chloride and saturated brine. The solution was dried (MgSO$_4$) and evaporated. The obtained crystals were washed with ethyl acetate to afford the title compound 0.447 g(76%). mp 212–213° C.

Example 7

Preparation of 4-oxo-N-[4-[(4-oxo-1-piperidinyl)methyl]phenyl]-4H-1-benzopyran-2-carboxamide To a solution of 4-oxo-4H-1-benzopyran-2-carboxylic acid (0.298 g), 1-(4-aminobenzyl)-4-oxopiperidine (0.348 g) and 1-ethyl-3-(3-dimethylaminopropyl)carbodiimide hydrochloride (0.372 g) in DMF (6 ml) was added 1-hydroxybenzotriazole (HOBt) (0.262 g), and the mixture was stirred at room temperature for 14 hours. The reaction solution was poured into water and extracted with a mixture solution of ethyl acetate and THF. The extract was washed with an aqueous solution of sodium hydrogencarbonate, an aqueous solution of ammonium chloride and saturated brine. The solution was dried (MgSO$_4$) and evaporated. The obtained crystals were recrystallized from ethyl acetate to afford the title compound 0.113 g(19%). mp 183–185° C.

Example 8

Preparation of 4-oxo-N-[4-[(1,3-thiazolidin-3-yl)methyl]phenyl]-4H-1-benzopyran-2-carboxamide To a solution of 4-oxo-4H-1-benzopyran-2-carboxylic acid (0.28 g), 1-(4-aminobenzyl)-1,3-thiazolidine (0.25 g) and 1-ethyl-3-(3-dimethylaminopropyl)carbodiimide hydrochloride(0.293 g) in DMF(6 ml) was added 1-hydroxybenzotriazole (HOBt) (0.2 g), and the mixture was stirred at room temperature for 14 hours. The reaction solution was poured into water and extracted with a mixture solution of ethyl acetate and THF. The extract was washed with an aqueous solution of sodium hydrogencarbonate, an aqueous solution of ammonium chloride and saturated brine. The solution was dried (MgSO$_4$) and evaporated. The obtained crystals were recrystallized from ethyl acetate to afford the title compound 0.347 g(64%). mp 203–204° C.

Example 9

Preparation of N-[4-[(1-piperazinyl)methyl]phenyl]-4-oxo-4H-1-benzopyran-2-carboxamide To a solution of 4-[4-[(4-oxo-4H-1-benzopyran-2-carbonyl)amino]benzyl]piperazine-1-carboxylic acid tert-butyl ester (0.2 g) in dichloromethane was dropwise added 4N hydrochloric acid ethyl acetate solution (3 ml). The reaction solution was stirred for 3 days and then concentrated. The residue was dissolved in 2N sodium hydroxide and extracted with a mixture solution of ethyl acetate-THF. The extract was washed with an aqueous solution of sodium hydrogencarbonate and saturated brine, dried (MgSO$_4$) and evaporated. The precipitated crystals were collected by filtration and washed with isopropyl ether to afford the title compound 0.09 g (59%). mp 138–140° C.

Example 10

Preparation of 4-[4-[(4-oxo-4H-1-benzopyran-2-carbonyl)amino]benzyl]piperazine-1-carboxylic acid tert-butyl ester To a solution of 4-oxo-4H-1-benzopyran-2-carboxylic acid (0.46 g) and 3-drops of DMF in THF (30 ml) was added oxalyl chloride (0.32 ml) under ice cooling, and the mixture was stirred at 0° C. for an hour. The reaction solution was concentrated under reduced pressure and the residue was dissolved in THF (20 ml). To the mixture was added 4-(4-aminobenzylpiperazine-1-carboxylic acid tert-butyl ester (0.7 g) and triethyl amine (0.84 ml) successively, and the mixture was stirred at room temperature for 14 hours. The reaction solution was poured into water and extracted with ethyl acetate. The extract was washed with an aqueous solution of sodium hydrogencarbonate, an aqueous solution of ammonium chloride and saturated brine, dried (MgSO$_4$) and evaporated. The residue was crystallized from isopropyl ether to afford the title compound 0.64 g(58%). mp 197–199° C.

Example 11

Preparation of N-[4-[(2,5-dioxo-1-imidazolidinyl)methyl]phenyl]-4-oxo-4H-1-benzopyran-2-carboxamide To a solution of 4-oxo-4H-1-benzopyran-2-carboxylic acid(0.4 g), 4-(2,5-dioxo-1-imidazolidinyl)methylaniline (0.561 g) and 1-ethyl-3-(3-dimethylaminopropyl) carbodiimide hydrochloride (0.805 g) in DMF was added 1-hydroxybenzotriazole (HOBt) (0.426 g), and the mixture was stirred at room temperature for 14 hours. The reaction solution was poured into a mixture of water and ethyl acetate and the crystals were collected by filtration. The obtained crystals were recrystallized from DMF-ethanol to afford the title compound 0.530 g (67%). mp 258–261° C.

Example 12

Preparation of N-[4-[(3-methyl-2,5-dioxo-1-imidazolidinyl)methyl]phenyl]-4-oxo-4H-1-benzopyran-2-carboxamide To a solution of 4-oxo-4H-1-benzopyran-2-carboxylic acid (0.28 g), 3-(4-aminobenzyl)-1-methylhydantoin (0.323 g) and 1-ethyl-3-(3-dimethylaminopropyl)carbodiimide hydrochloride (0.294 g) in DMF (10ml) was added 1-hydroxybenzotriazole (HOBt)(0.2 g), and the mixture was stirred at room temperature for 14 hours. The reaction solution was poured into water and extracted with a mixture solution of ethyl acetate and THF. The extract was washed with an aqueous solution of sodium hydrogencarbonate and saturated brine, dried ($MgSO_4$) and evaporated. The residue was recrystallized from THF-ethyl acetate to afford the title compound 0.369 g(64%). mp 195–196° C.

Example 13

Preparation of N-[4-(2,4-dioxo-1,3-oxazolidin-3-yl) methyl]phenyl]-4-oxo-4H-1-benzopyran-2-carboxamide To a solution of 4-oxo-4H-1-benzopyran-2-carboxylic acid (0.28 g), 1-(4-aminobenzyl)-2,4-dioxooxazolidine (0.304 g) and 1-ethyl-3-(3-dimethylaminopropyl) carbodiimide hydrochloride(0.294 g) in DMF (10 ml) was added 1-hydroxybenzotriazole (HOBt) (0.2 g), and the mixture was stirred at room temperature for 14 hours. The reaction solution was poured into water and extracted with a mixture solution of ethyl acetate and THF. The extract was washed with an aqueous solution of sodium hydrogencarbonate, an aqueous solution of ammonium chloride and saturated brine, dried ($MgSO_4$) and evaporated. The obtained crystals were recrystallized from ethyl acetate to afford the title compound 0.451 g(64%). mp 261–262° C.

Example 14

Preparation of N-[4-[2,4-dioxo-1,3-thiazolidin-3-yl] methyl]phenyl]-4-oxo-4H-1-benzopyran-2-carboxamide To a solution of 4-oxo-4H-1-benzopyran-2-carboxylic acid (0.4 g), 3-(4-aminobenzyl)-2,4-dioxo-1,3-thiazolidine (0.47 g) and 1-ethyl-3-(3-dimethylaminopropyl) carbodiimide hydrochloride (0.805 g) in DMF (20 ml) was added 1-hydroxybenzotriazole (HOBt)(0.426 g), and the mixture was stirred at room temperature for 14 hours. The reaction solution was poured into a mixture of water and ethyl acetate and extracted with ethyl acetate. The extract was washed with an aqueous solution of 1N hydrochloric acid and an aqueous solution of sodium hydrogencarbonate and saturated brine, dried ($MgSO_4$) and evaporated. The obtained crystals were washed with isopropyl ether/hexane to afford the title compound 0.725 g(88%). mp 206–208° C.

Example 15

Preparation of N-[4-[(3-methyl-2,4-dioxo-1,3-thiazolidin-5-yl)methyl]phenyl]-4oxo-4H-1-benzopyran-2-carboxamide To a suspension solution of N-[4-[(2,4-dioxo-1,3-thiazolidine-5-yl)methyl]phenyl]-4-oxo-4H-1-benzopyran-2-carboxamide (0.394 g) in THF (30 ml) was added an excess amount of diazomethane/ether solution which was separately prepared at 0° C. and the mixture was stirred at room temperature for 3 hours. The reaction solution was concentrated, diluted with a mixture solution of THF-ethyl acetate, washed with a solution of ammonium chloride and saturated brine and dried ($MgSO_4$). Removal of the solvent gave the title compound 0.36 g(88%). mp 214–216° C.

Example 16

Preparation of N-[4-[(2,4-dioxo-1,3-thiazolidin-5-yl) methyl]phenyl]-5-hydroxy-4-oxo-4H-1-benzopyran-2-carboxamide To a solution of 5-hydroxy-4-oxo-4H-1-benzopyran-2-carboxylic acid (0.23 g), 5-(4-aminobenzyl)-2,4-dioxo-1,3-thiazolidine (0.647 g) and 1-ethyl-3-(3-dimethylaminopropyl)carbodiimide hydrochloride (0.932 g) in DMF (20 ml) was added 1-hydroxybenzotriazole (HOBt) (0.492 g), and the mixture was stirred at room temperature for 14 hours. The reaction solution was poured into water and extracted with a mixture of ethyl acetate and THF. The extract was washed with diluted hydrochloric acid and saturated brine and dried ($MgSO_4$). The solvent was evaporated. The obtained crystals were recrystallized from THF-acetone to afford the title compound 0.636 g(64%). mp 284–286° C.

Example 17

Preparation of 5,6-dihydroxy-N-[4-[2,4-dioxo-1,3-thiazolidin-5-yl]methyl]phenyl]-4-oxo-4H-1-benzopyran-2-carboxamide To a solution of 5,6-dihydroxy-4-oxo-4H-1-benzopyran-2-carboxylic acid (0.325 g), 5-(4-aminobenzyl)-2,4-dioxo-1,3-thiazolidine (0.321 g) and 1-ethyl-3-(3-dimethylaminopropyl)carbodiimide hydrochloride (0.311 g) in DMF(8 ml) was added 1-hydroxybenzotriazole (HOBt) (0.22 g), and the mixture was stirred at room temperature in 16 hours. The reaction solution was poured into water and extracted with a mixture of ethyl acetate and THF. The extract was washed with an aqueous solution of sodium hydrogencarbonate, an aqueous solution of ammonium chloride and saturated brine, dried ($MgSO_4$) and evaporated. The obtained crystals were recrystallized from ethyl acetate to afford the title compound 0.1789 g (29%). mp 280° C. (decomposed)

Example 18

Preparation of 5,7-dihydroxy-N-[4-[(2,4-dioxo-1,3-thiazolidin-5-yl)methyl]phenyl-4-oxo-4H-1-benzopyran-2-carboxamide To a solution of 5,7-dihydroxy-4-oxo-4H-1-benzopyran-2-carboxylic acid (0.069 g), 5-(4-aminobenzyl)-2,4-dioxo-1,3-thiazolidine (0.069 g) and 1-ethyl-3-(3-dimethylaminopropyl)carbodiimide hydrochloride (0.66 g) in DMF (8 ml) was added 1-hydroxybenzotriazole (HOBt) (0.053 g), and the mixture was stirred at room temperature for 15 hours. The reaction solution was poured into water and the precipitated crystals were collected by filtration. The obtained crystals were recrystallized from THF-methanol to afford the title compound 0.11 g (83%). mp>300° C.

Example 19

Preparation of N-[4-[(2,4-dioxo-1,3-thiazolidin-5-yl) methyl]phenyl]-5-hydroxy-7-methoxy-4-oxo-4H-1-benzopyran-2-carboxamide To a solution of 5-hydroxy-7-methoxy-4-oxo-4H-1-benzopyran-2-carboxylic acid (0.15 g), 5-(4-aminobenzyl)-

2,4-dioxo-1,3-thiazolidine (0.141 g) and 1-ethyl-3-(3-dimethylaminopropyl)carbodiimide hydrochloride (0.134 g) in DMF (15 ml) was added 1-hydroxybenzotriazole (HOBt) (0.107 g) in DMF (15 ml) and the mixture was stirred at room temperature for 15 hours. The reaction solution was poured into water and extracted with ethyl acetate. The extract was washed with an aqueous solution of sodium hydrogencarbonate and saturated brine, dried (MgSO$_4$) and evaporated. The obtained crystals were recrystallized from THF-ethyl acetate to afford the title compound 0.22 g (79%). mp 255–256° C.

Example 20

Preparation of N-[4-[(2,4-dioxo-1,3-thiazolidin-5-yl)methyl]phenyl]-5-hydroxy-7-methyl-4-oxo-4H-1-benzopyran-2-carboxamide To a solution of 5-hydroxy-7-methyl-4-oxo-4H-1-benzopyran-2-carboxylic acid (0.204 g), 5-(4-aminobenzyl)-2,4-dioxo-1,3-thiazolidine (0.206 g) and 1-ethyl-3-(3-dimethylaminopropyl)carbodiimide hydrochloride (0.198 g) in DMF(6 ml) was added 1-hydroxybenzotriazole (HOBt) and the mixture was stirred at room temperature for 14 hours. The reaction solution was poured into water and extracted with a mixture of ethyl acetate and THF. The extract was washed with an aqueous solution of sodium hydrogencarbonate, an aqueous solution of ammonium chloride and saturated brine, dried (MgSO$_4$) and evaporated. The obtained crystals were recrystallized from THF to afford the title compound 0.269 g (68%). mp 290° C. (decomposed)

Example 21

Preparation of N-[4-[(2,4-dioxo-1,3-thiazolidine-5-yl)methyl]phenyl]-5-methoxy-7-methyl-4-oxo-4H-1-benzopyran-2-carboxamide To a solution of 5-methoxy-7-methyl-4-oxo-4H-1-benzopyran-2-carboxylic acid (0.205 g), 5-(4-aminobenzyl)-2,4-dioxo-1,3-thiazoline (0.195 g) and ethyl-3-(3-dimethylaminopropyl)carbodiimide (0.186 g) in DMF (6 ml) was added 1-hydroxybenzotriazole (HOBt) (0.13 g), and the mixture was stirred at room temperature for 16 hours. The reaction solution was poured into water and extracted with a mixture of ethyl acetate and THF. The extract was washed with an aqueous solution of sodium hydrogencarbonate, an aqueous solution of ammonium chloride and saturated brine, dried (MgSO$_4$) and evaporated. The obtained crystals were recrystallized from THF to afford the title compound 0.269 g(70%). mp 267–269° C.

Example 22

Preparation of 6,7-dihydroxy-N-[4-[(2,4-dioxo-1,3-thiazolidin-5-yl)methyl]phenyl]-4-oxo-4H-1-benzopyran-2-carboxamide To a solution of 6,7-dihydroxy-4-oxo-4H-1-benzopyran-2-carboxylic acid (0.15 g), 5-(4-aminobenzyl)-2,4-dioxo-1,3-thiazolidine (0.15 g) and 1-ethyl-3-(3-dimethylaminopropyl)carbodiimide hydrochloride (0.145 g) in DMF (15 ml) was added 1-hydroxybenzotriazole (HOBt) (0.115 g), and the mixture was stirred at room temperature for 15 hours. The reaction solution was diluted with a mixture solution of ethyl acetate and THF, washed with an aqueous solution of sodium hydrogencarbonate and saturated brine, dried (MgSO$_4$) and evaporated. The obtained crystals were recrystallized from ethyl acetate-n-hexane to afford the title compound 0.097 g(34%). mp >300° C.

Example 23

Preparation of N-[4-[(2,4-dioxo-1,3-thiazolidin-5-yl)methyl]phenyl]-5,7-dimethoxy-4-oxo-4H-1-benzopyran-2-carboxamide To a solution of 5,7-dimethoxy-4-oxo-4H-1-benzopyran-2-carboxylic acid (0.099 g), 5-(4-aminobenzyl)-2,4-dioxo-1,3-thiazolidine (0.088 g) and 1-ethyl-3-(3-dimethylaminopropyl)carbodiimide hydrochloride (0.084 g) in DMF (10 ml) was added 1-hydroxybenzotriazole (HOBt) (0.067 g), and the mixture was stirred at room temperature for 15 hours. The reaction mixture was diluted with a mixture solution of ethyl acetate and THF, washed with an aqueous solution of sodium hydrogencarbonate and saturated brine, dried (MgSO$_4$) and evaporated. The obtained crystals were recrystallized from DMF-water to afford the title compound 0.129 g(72%). mp >300° C.

Example 24

Preparation of N-[4-[(2,4-dioxo-1,3-thiazolidin-5-yl)methyl]phenyl]-5-methoxy-4-oxo-4H-1-benzopyran-2-carboxamide To a solution of 5-methoxy-4-oxo-4H-1-benzopyran-2-carboxylic acid (0.101 g), 5-(4-aminobenzyl)-2,4-dioxo-1,3-thiazolidine (0.11 g) and 1-ethyl-3-(3-dimethylaminopropyl)carbodiimide hydrochloride (0.097 g) in DMF (10 ml) was added 1-hydroxybenzotriazole (HOBt) (0.078 g), and the mixture was stirred at room temperature for 15 hours. The reaction solution was poured into water and extracted with a mixture solution of ethyl acetate and THF. The extract was washed with an aqueous solution of sodium hydrogencarbonate and saturated brine, dried (MgSO$_4$) and evaporated. The obtained crystals were recrystallized from ethyl acetate-n-hexane to afford the title compound 0.108 g(56%). mp 293–294° C.

Example 25

Preparation of N-[4-[(2,4-dioxo-1,3-thiazolidin-5-yl)methyl]phenyl]-5-hydroxy-4-oxo-10-propyl-6,7,8,9-tetrahydro-4H-naphtho[2,3-b]pyran-2-carboxamide To a solution of 5-hydroxy-4-oxo-10-propyl-6,7,8,9-tetrahydro-4H-naphtho[2,3-b]pyran-2-carboxylic acid (0.2 g), 5-(4-aminobenzyl)-2,4-dioxo-1,3-thiazolidine (0.154 g) and 1-ethyl-3-(3-dimethylaminopropyl)carbodiimide hydrochloride (0.14 g) in DMF (12 ml) was added 1-hydroxybenzotriazole (HOBt)(0.112 g), and the mixture was stirred at room temperature for 15 hours. The reaction solution was diluted with a mixture solution of ethyl acetate and THF, washed with an aqueous solution of sodium hydrogencarbonate and saturated brine, dried (MgSO$_4$) and evaporated. The obtained crystals were recrystallized from ethyl acetate-n-hexane to afford the title compound 0.281 g(84%). mp 224–225° C.

Example 26

Preparation of 6,8-dibromo-N-[4-[(2,4-dioxo-1,3-thiazolidin-5-yl)methyl]phenyl]-5-hydroxy-4-oxo-4H-1-benzopyran-2-carboxamide To a solution of 6,8-dibromo-5-hydroxy-4-oxo-4H-1-benzopyran-2-carboxylic acid (0.364 g), 5-(4- aminobenzyl)-2,4-dioxo-1,3-thiazolidine (0.23 g) and 1-ethyl-3-(3-dimethylaminopropyl)carbodiimide hydrochloride (0.383 g) in DMF (15 ml) was added 1-hydroxybenzotriazole (HOBt) (0.203 g), and the mixture was stirred at room temperature for 14 hours. The reaction solution was poured into water and extracted with a mixture of ethyl acetate and THF. The extract was washed with diluted hydrochloric acid, an aqueous solution of sodium hydrogencarbonate and saturated brine, dried (MgSO$_4$) and evaporated. The residue was purified by silica gel column chromatography to afford the title compound 0.07 g(11%). mp 283–285° C.

Example 27

Preparation of N-[4-[(2,4-dioxo-1,3-thiazolidin-5-yl) methyl]phenyl-5,6-methylenedioxy-4-oxo-4H-1-benzopyran-2-carboxamide To a solution of 5,6-methylenedioxy-4-oxo-1-benzopyran-2-carboxylic acid (0.33 g), 5-(4-aminobenzyl)-2,4-dioxo-1,3-thiazolidine (0.306 g) and 1-ethyl-3-(3-dimethylaminopropyl)carbodiimide hydrochloride (0.31 g) in DMF (10 ml) was added 1-hydroxybenzotriazole (HOBt) (0.19 g), and the mixture was stirred at room temperature for 14 hours. The reaction solution was poured into water and extracted with a mixture of ethyl acetate and THF. The extract was washed with an aqueous solution of sodium hydrogencarbonate, an aqueous solution of ammonium chloride and saturated brine, dried (MgSO$_4$) and evaporated. The obtained crystals were recrystallized from THF to afford the title compound 0.309 g (50%). mp>300° C.

Example 28

Preparation of N-[4-[(2,4-dioxo-1,3-thiazolidin-5-yl) methyl]phenyl]-6-methyl-4-oxo-4H-1-benzopyran-2-carboxamide To a solution of 6-methyl-4-oxo-4H-1-benzopyran-2-carboxylic acid (0.205 g), 5-(4-aminobenzyl-2,4-dioxo-1,3-thiazolidine (0.23 g) and 1-ethyl-3-(3-dimethylaminopropyl)carbodiimide hydrochloride (0.383 g) in DMF (10 ml) was added 1-hydroxybenzotriazole (HOBt) (0.203 g), and the mixture was stirred at room temperature for 14 hours. The reaction solution was poured into water and extracted with a mixture solution of ethyl acetate and THF. The extract was washed with diluted hydrochloric acid, an aqueous solution of sodium hydrogencarbonate and saturated brine, dried (MgSO$_4$) and evaporated. The obtained crystals were recrystallized by THF-ethanol to afford the title compound 0.28 g (69%). mp 260° C. (decomposed)

Example 29

Preparation of N-[4-[(2,4-dioxo-1,3-thiazolidin-5-yl) methyl]phenyl]-8-methyl-4-oxo-4H-1-benzopyran-2-carboxamide To a solution of 8-methyl-4-oxo-4H-1-benzopyran-2-carboxylic acid (0.207 g), 5-(4-aminobenzyl)-2,4-dioxo-1,3-thiazolidine (0.222 g) and 1-ethyl-3-(3-dimethylaminopropyl)carbodiimide hydrochloride (0.383 g) in DMF (10 ml) was added 1-hydroxybenzotriazole (HOBt) (0.203 g), and the mixture was stirred at room temperature for 14 hours. The reaction solution was poured into water and extracted with a mixture solution of ethyl acetate and THF. The extract was washed with diluted hydrochloric acid, an aqueous solution of sodium hydrogencarbonate and saturated brine, dried (MgSO$_4$) and evaporated to afford the title compound 0.193 g (47%). mp 305–307° C.

Example 30

Preparation of 6-bromo-N-[4-[(2,4-dioxo-1,3-thiazolidin-5-yl)methyl]phenyl]-4-oxo-4H-1-benzopyran-2-carboxamide To a solution of 6-bromo-4-oxo-4H-1-benzopyran-2-carboxylic acid (0.0269 g), 5-(4-aminobenzyl)-2,4-dioxothiazolidine (0.23 g) and 1-ethyl-3-(3-dimethylaminopropyl)carbodiimide hydrochloride (0.383 g) in DMF (10 ml) was added 1-hydroxybenzotriazole (HOBt) (0.203 g), and the mixture was stirred at room temperature for 14 hours. The reaction solution was poured into water and extracted with a mixture solution of ethyl acetate and THF. The extract was washed with diluted hydrochloric acid, an aqueous solution of sodium hydrogencarbonate and saturated brine, dried (MgSO$_4$) and evaporated. The obtained crystals were recrystallized from THF-ethanol to afford the title compound 0.266 g (56%). mp 281–285° C.

Example 31

Preparation of N-[4-[(2,4-dioxo-1,3-thiazolidin-5-yl) methyl]phenyl]-6-fluoro-4-oxo-4H-1-benzopyran-2-carboxylic acid To a solution of 6-fluoro-4-oxo-4H-1-benzopyran-2-carboxylic acid (0.214 g), 5-(4-aminobenzyl)-2,4-dioxo-1,3-thiazolidine (0.266 g) and 1-ethyl-3-(3-dimethylaminopropyl)carbodiimide hydrochloric acid (0.244 g) in DMF (4 ml) was added 1-hydroxybenzotriazole (HOBt) (0.514 g), and the mixture was stirred at room temperature for 60 hours. The reaction solution was poured into water and the precipitated crystals were washed with water and ethanol, isopropyl ether to afford the title compound 0.39 g (93%). mp 285–287° C.

Example 32

Preparation of 8-bromo-N-[4-[(2,4-dioxo-1,3-thiazolidin-5-yl)methyl]phenyl]-4-oxo-4H-1-benzopyran-2-carboxamide To a solution of 8-bromo-4-oxo-4H-1-benzopyran-2-carboxylic acid (0.269 g) and DMF (3 drops) in THF solution was added oxalyl chloride (0.14 ml) under ice cooling, and the mixture was stirred at 0° C. for an hour. The reaction solution was concentrated under reduced pressure and the residue was dissolved in THF (10 ml). To the mixture was added 5-(4-aminobenzyl)-2,4-dioxo-1,3-thiazoline (0.333 g), triethylamine (0.42 ml), successively and the mixture was stirred at room temperature for 14 hours. The reaction solution was poured into water and extracted with a mixture solution of ethyl acetate-THF. The extract was washed with diluted hydrochloric acid, an aqueous solution of sodium hydrogencarbonate and saturated brine, dried (MgSO$_4$) and evaporated to afford the title compound 0.216 g(46%). mp 293–295° C.

Example 33

Preparation of N-[4-[(2,4-dioxo-1,3-thiazolidin-5-yl) methyl]phenyl]-7-fluoro-4-oxo-4H-1-benzopyran-2-carboxamide To a solution of 7-fluoro-4-oxo-4H-1-benzopyran-2-carboxylic acid (0.207 g), 5-(4-aminobenzyl)-2,4-dioxo-1, 3-thiazolidine (0.223 g) and 1-ethyl-3-(3-dimethylaminopropyl)carbodiimide hydrochloride (0.321 g) in DMF (5 ml) was added 1-hydroxybenzotriazole (HOBt) (0.194 g), and the mixture was stirred at room temperature for 14 hours. The reaction solution was poured into water and extracted with a mixture solution of ethyl acetate and THF. The extract was washed with an aqueous solution of sodium hydrogencarbonate and saturated brine, dried (MgSO$_4$) and evaporated. The obtained crystals were recrystallized from ethyl acetate to afford the title compound 0.369 g(90%). mp 247–249° C.

Example 34

Preparation of N-4-[(2,4-dioxo-1,3-thiazolidin-5-yl)methyl]phenyl]-5-fluoro-4-oxo-4H-1-benzopyran-2-carboxamide To a solution of 5-fluoro-4-oxo-4H-1-benzopyran-2-carboxylic acid (0.213 g), 5-(4-aminobenzyl)-2,4-dioxo-1,3-thiazolidine (0.228 g) and 1-ethyl-3-(3-dimethylaminopropyl)carbodiimide hydrochloride (0.218 g) in DMF (5 ml) was added 1-hydroxybenzotriazole (HOBt) (0.155 g), and the mixture was stirred at room temperature for 14 hours. The reaction solution was poured into water and extracted with a mixture solution of ethyl acetate and THF. The extract was washed with diluted hydrochloric acid, an aqueous solution of sodium hydrogencarbonate and saturated brine, dried (MgSO$_4$) and evaporated. The obtained crystals were recrystallized from ethanol-isopropylether to afford the title compound 0.418 g(99%). mp 282–283° C.

Example 35

Preparation of 5,7-difluoro-N-[4-[(2,4-dioxo-1,3-thiazolidin-5-yl)methyl]phenyl]-4-oxo-4H-1-benzopyran-2-carboxamide To a solution of 5,7-difluoro-4-oxo-4H-1-benzopyran-2-carboxylic acid (0.246 g), 5-(4-aminobenzyl)-2,4-dioxo-1,3-thiazolidine (0.244 g) and 1-ethyl-3-(3-dimethylaminopropyl)carbodiimide hydrochloride (0.2313 g) in DMF (5 ml) was added 1-hydroxybenzotriazole (HOBt)(0.161 g), and the mixture was stirred at room temperature for 16 hours. The reaction solution was poured into water and extracted with a mixture solution of ethyl acetate and THF. The extract was washed with diluted hydrochloric acid, an aqueous solution of sodium hydrogencarbonate and saturated brine, dried (MgSO$_4$) and evaporated. The obtained crystals were recrystallized from THF to afford the title compound 0.44 g(89%). mp 280–282° C.

Example 36

Preparation of N-[4-(2,4-dioxo-1,3-thiazolidin-5-yl)methyl]phenyl]-8-phenyl-4-oxo-4H-1-benzopyran-2-carboxamide To a solution of 8-phenyl-4-oxo-4H-1-benzopyran-2-carboxylic acid (0.27 g), 5-(4-aminobenzyl)-2,4-dioxo-1,3-thiazolidine(0.23 g) and 1-ethyl-3-(3-dimethylaminopropyl) carbodiimide hydrochloride(0.38 g) in DMF (10 ml) was added 1-hydroxybenzotriazole (HOBt) (0.2 g), and the mixture was stirred at room temperature for 14 hours. The reaction solution was poured into water and extracted with a mixture solution of ethyl acetate and THF. The extract was washed with diluted hydrochloric acid, an aqueous solution of sodium hydrogencarbonate and saturated brine, dried (MgSO$_4$) and evaporated. The title compound was obtained as an amorphous powder 0.28 g(60%).

Example 37

Preparation of N-[4-(2,4-dioxo-1,3-thiazolidin-5-yl)methyl]phenyl]-7-phenyl-4-oxo-4H-1-benzopyran-2-carboxamide To a solution of 7-phenyl-4-oxo-4H-1-benzopyran-2-carboxylic acid (0.268 g), 5-(4-aminobenzyl)-2,4-dioxo-1,3-thiazolidine (0.223 g) and 1-ethyl-3-(3-dimethylaminopropyl)carbodiimide hydrochloride (0.218 g) in DMF (10 ml) was added 1-hydroxybenzotriazole (HOBt) (0.149 g), and the mixture was stirred at room temperature for 14 hours. The reaction solution was poured into water and extracted with a mixture of ethyl acetate and THF. The extract was washed with diluted hydrochloric acid, an aqueous solution of sodium hydrogencarbonate and saturated brine, dried (MgSO$_4$) and evaporated. The obtained crystals were recrystallized from THF-ethanol to afford the title compound 0.39 g (82%). mp 235–237° C.

Example 38

Preparation of N-[4-[(2,4-dioxo-1,3-oxazolidin-5-yl)methyl]phenyl]-5-hydroxy-4-oxo-4H-1-benzopyran-2-carboxamide To a solution of 5-hydroxy-4-oxo-4H-1-benzopyran-2-carboxylic acid (0.206 g) 5-(4-aminobenzyl)-2,4-dioxo-1,3-oxazolidine (0.21 g) and 1-ethyl-3-(3-dimethylaminopropyl) carbodiimide hydrochloride (0.383 g) in DMF was added 1-hydroxybenzotriazole (HOBt) (0.203 g), and the mixture was stirred at room temperature for 14 hours. The reaction solution was poured into water and extracted with a mixture of ethyl acetate and THF. The extract was washed with an aqueous solution of sodium hydrogencarbonate and saturated brine, dried (MgSO$_4$) and evaporated. The obtained residue was purified by silica gel column chromatography to afford the title compound 0.216 g(55%). mp 298–300° C.

Example 39

Preparation of 5-hydroxy-N-[4-(4-morpholinylmethyl)phenyl]-4-oxo-4H-1-benzopyran-2-carboxamide To a solution of 5-hydroxy-4-oxo-4H-1-benzopyran-2-carboxylic acid (0.3 g), 4-(4-aminobenzyl)morpholine (0.308 g) and 1-ethyl-3-(3-dimethylaminopropyl) carbodiimide hydrochloride (0.56 g) in DMF (20 ml) was added 1-hydroxybenzotriazole (HOBt) (0.296 g), and the mixture was stirred at room temperature for 14 hours. The reaction solution was poured into water and extracted with a mixture of ethyl acetate and THF. The extract was washed with an aqueous solution of sodium hydroxide and saturated brine, dried (MgSO$_4$) and evaporated. The obtained oily product was crystallized from isopropyl ether to afford the title compound 0.4 g(72%). mp 200–202° C.

Example 40

Preparation of 5,6-dihydroxy-N-[4-[(4-morpholinyl)methyl]phenyl]-4-oxo-4H-1-benzopyran-2-carboxamide To a solution of 5,6-dihydroxy-4-oxo-4H-1-benzopyran-2-carboxylic acid (0.169 g), 4-(4-aminobenzyl)morpholine (0.146 g) and 1-ethyl-3-(3-dimethylaminopropyl)

carbodiimide hydrochloride (0.16 g) in DMF (6 ml) was added 1-hydroxybenzotriazole (HOBt) (0.12 g), and the mixture was stirred at room temperature for 16 hours. The reaction solution was poured into water and extracted with a mixture of ethyl acetate and THF. The extract was washed with an aqueous solution of sodium hydrogencarbonate, an aqueous solution of ammonium chloride and saturated brine, dried ($MgSO_4$) and evaporated. The obtained crystals were recrystallized from ethyl acetate to afford the title compound 0.05 g(16%). mp 235–237° C.

Example 41

Preparation of 5,7-dihydroxy-N-[4-[(4-morpholinyl) methyl]phenyl]-4-oxo-4H-1-benzopyran-2-carboxamide To a solution of 5,7-dihydroxy-4-oxo-4H-1-benzopyran-2-carboxylic acid (0.225 g), 4-(4-aminobenzyl)morpholine (0.198 g) and 1-ethyl-3-(3-dimethylaminopropyl) carbodiimide hydrochloride (0.227 g) in DMF (6 ml) was added 1-hydroxybenzotriazole (HOBt) (0.154 g), and the mixture was stirred at room temperature for 14 hours. The reaction solution was poured into water. The precipitated crystals were collected by filtration and washed with ethanol and water to afford the title compound 0.240 g(60%). mp 207–209° C.

Example 42

Preparation of N-methyl-N-[4-[(4-morpholinyl) methyl]phenyl]-4-oxo-4H-1-benzopyran-2-carboxamide hydrochloride To a solution of 4-oxo-4H-1-benzopyran-2-carboxylic acid (0.19 g) and DMF (3 drops) in THF was added oxalyl chloride (0.13 ml) under ice cooling, and the mixture was stirred at 0° C. for an hour. The reaction solution was concentrated under reduced pressure and the residue was dissolved in THF (10 ml). To the mixture solution was added 4-(4-methylaminobenzyl) morpholine (0.203 g) and triethylamine (0.28 ml) successively, and the mixture was stirred at room temperature for 14 hours. The reaction solution was poured into water and extracted with a mixture of ethyl acetate and THF. The extract was washed with an aqueous solution of sodium hydrogencarbonate and saturated brine, dried ($MgSO_4$) and evaporated. The obtained residue was purified by silica gel column chromatography and the obtained oily product (0.4 g) was dissolved into ethyl acetate (2 ml). To the mixture was dropwise added 4N hydrochloric acid ethyl acetate solution (0.5 ml) and the precipitated crystals were collected by filtration to afford the title compound 0.315 g (76%). mp 230° C. (decomposed)

Example 43

Preparation of 5-hydroxy-N-methyl-N-[4-(4-morpholinylmethyl)phenyl]-4-oxo-4H-1-benzopyran-2-carboxamide hydrochloride To a solution of 5-hydroxy-4-oxo-4H-1-benzopyran-2-carboxylic acid (0.206 g) and DMF (3 drops) in THF solution was added oxalyl chloride (0.22 ml) under ice cooling and the mixture was stirred at 0° C. for an hour. The reaction solution was concentrated under reduced pressure and the residue was dissolved in THF (10 ml). To the mixture was added 4-(4-methylaminobenzyl)morpholine (0.203 g) and triethylamine (0.28 ml) successively, and the mixture was stirred at room temperature for 14 hours. The reaction solution was poured into water and extracted with a mixture solution of ethyl acetate-THF. The extract was washed with diluted hydrochloric acid, an aqueous solution of sodium hydrogencarbonate and saturated brine, dried ($MgSO_4$) and evaporated. The obtained crystals were washed with isopropyl ether to afford the title compound 0.261 g(69%). mp 175–176° C.

Example 44

Preparation of 5-hydroxy-4-oxo-N-[4-(1-piperidinylmethyl)phenyl]-4H-1-benzopyran-2-carboxamide To a solution of 5-hydroxy-4-oxo-4H-1-benzopyran-2-carboxylic acid (0.206 g), 1-(4-aminobenzyl)piperidine (0.19 g) and 1-ethyl-3-(3-dimethylaminopropyl) carbodiimide hydrochloride (0.383 g) in DMF (15 ml) was added 1-hydroxybenzotriazole (HOBt) (0.203 g), and the mixture was stirred at room temperature for 14 hours. The reaction solution was poured into water and extracted with a mixture of ethyl acetate and THF. The extract was washed with an aqueous solution of sodium hydrogencarbonate and saturated brine, dried ($MgSO_4$) and evaporated. The obtained crystals were washed with isopropyl ether to afford the title compound 0.261 g(69%). mp 175–176° C.

Example 45

Preparation of 5-hydroxy-4-oxo-N-[4-[[4-(methylsulfonyl)-1-piperazinyl]methyl]phenyl]-4H-1-benzopyran-2-carboxamide To a solution of 5-hydroxy-4-oxo-4H-1-benzopyran-2-carboxylic acid (0.206 g), 4-[[4-(methylsulfonyl)-1-piperazinyl]methyl]aniline (0.19 g) and 1-ethyl-3-(3-dimethylaminopropyl)carbodiimide hydrochloride (0.383 g) in DMF (15 ml) was added 1-hydroxybenzotriazole (HOBt), and the mixture was stirred at room temperature for 14 hours. The reaction solution was poured into water and extracted with a mixture of ethyl acetate and THF. The extract was washed with an aqueous solution of sodium hydrogencarbonate and saturated brine, dried ($MgSO_4$) and evaporated. The obtained crystals were washed with isopropyl ether to afford the title compound 0.261 g(69%). mp 175–176° C.

Example 46

Preparation of N-[4-[[(4-formyl)-1-piperazinyl] methyl]phenyl]-5-hydroxy-4-oxo-4H-1-benzopyran-2-carboxamide To a solution of 5-hydroxy-4-oxo-4H-1-benzopyran-2-carboxylic acid (0.113 g), 4-(4-aminobenzyl)-1-piperazinecarbaldehyde(0.223 g) and 1-ethyl-3-(3-dimethylaminopropyl)carbodiimide hydrochloride (0.125 g) in DMF (5 ml) was added 1-hydroxybenzotriazole (HOBt) (0.112 g), and the mixture was stirred at room temperature for two days. The reaction solution was poured into water and extracted with a mixture of ethyl acetate and THF. The extract was washed with an aqueous solution of sodium hydrogencarbonate, an aqueous solution of ammonium chloride and saturated brine, dried ($MgSO_4$) and evaporated to afford the title compound 0.053 g (23%). mp 240° C. (decomposed)

Example 47

Preparation of N-[4-[(2,4-dioxothiazolidin-5-yl) methyl]phenyl]-5-acetoxy-4-oxo-4H-1-benzopyran-2-carboxamide To a solution of N-[4-[(2,4-dioxothiazolidine-5-yl) methyl]phenyl]-5-hydroxy-4-oxo-4H-1-benzopyran-2- carboxamide (0.329 g) and acetic anhydride (0.23 ml) in ethyl acetate (30 ml) was added trifluoromethanesulfonic acid trimethylsilyl (TMSOTf) (0.43 ml), and the mixture was stirred at room temperature for 14 hours. The reaction solution was poured into water and extracted with a mixture of ethyl acetate and THF. The extract was washed with an aqueous solution of sodium hydrogencarbonate and saturated brine, dried (MgSO$_4$) and evaporated to afford the title compound 0.035 g (95%). mp 257–260° C.

Example 48

Preparation of N-[4-[(2,4-dioxothiazolidine-5-yl)methyl]phenyl]-5-butyryloxy-4-oxo-4H-1-benzopyran-2-carboxamide To a solution of 5-butyryloxy-4-oxo-4H-1-benzopyran-2-carboxylic acid (0.28 g) and DMF (3 drops) in THF solution (10 ml) was added oxalyl chloride (0.14 ml) under ice cooling and the mixture was stirred for an hour. The reaction solution was concentrated. THF (10 ml) was added to the mixture. Then, to the mixture was added 5-(4-aminobenzyl)-2,4-dioxothiazolidine (0.24 g) and triethylamine (0.42 ml) in THF solution (5 ml), and the mixture was stirred at room temperature for 14 hours. The reaction solution was poured into water and extracted with a mixture solution of ethyl acetate-THF. The extract was washed with diluted hydrochloric acid, an aqueous solution of sodium hydrogencarbonate and saturated brine, dried (MgSO$_4$) and evaporated. The obtained crystals were recrystallized from THF-isopropyl ether to afford the title compound 0.32 g(67%). mp 249–250° C.

Example 49

Preparation of N-[4-[(2,4-dioxothiazolidin-5-yl)methyl]phenyl]-5-isobutyryloxy-4-oxo-4H-1-benzopyran-2-carboxamide To a solution of 5-isobutyloxy-4-oxo-4H-1-benzopyran-2-carboxylic acid (0.28 g) and DMF (3 drops) in THF solution (10 ml) was added oxalyl chloride (0.14 ml) under ice cooling and the mixture was stirred for an hour. The reaction solution was concentrated. THF (10 ml) was added to the mixture. Then, to the mixture was added 5-(4-aminobenzyl)-2,4-dioxothiazolidine (0.24 g) and triethylamine (0.42 ml) in THF solution (5 ml), and the mixture was stirred at room temperature for 14 hours. The reaction solution was poured into water and extracted with a mixture solution of ethyl acetate-THF. The extract was washed with diluted hydrochloric acid, an aqueous solution of sodium hydrogencarbonate and saturated brine, dried (MgSO$_4$) and evaporated. The obtained crystals were recrystallized from THF-isopropyl ether to afford the title compound 0.18 g(38%). mp 273–275° C.

Example 50

Preparation of diethylcarbamic acid 2-[4-(2,4-dioxothiazolidin-5-ylmethyl)phenyl]carbamoyl]-4-oxo-4H-1-benzopyran-5-yl ester To a solution of the corresponding carboxylic acid (0.15 g), 5-(4-aminobenzyl)-2,4-dioxothiazolidine (0.22 g) and 1-ethyl-3-(3-dimethylaminopropyl)carbodiimide hydrochloride (0.29 g) in DMF (10 ml) was added 1-hydroxybenzotriazole (0.10 g), and the mixture was stirred at room temperature for 14 hours. The reaction solution was poured into water and extracted with a mixture of ethyl acetate and THF. The extract was washed with diluted hydrochloric acid, water, an aqueous solution of sodium hydrogencarbonate and saturated brine, dried (MgSO$_4$) and evaporated to afford the title compound 0.015 g (57%). mp 228–230° C.

Example of pharmaceutical substance 1

The compound (10 mg) prepared in Example 1, lactose (90 mg), fine crystalline cellulose (70 mg) and magnesium stearate (5 mg) are mixed and formulated into granules. Magnesium stearate (5 mg) was added thereto, and the whole is included in a gelatin capsule.

Example of pharmaceutical substance 2

The compound (10 mg) prepared in Example 16, lactose (35 mg), corn starch (150 mg), fine crystalline cellulose (20 mg) and magnesium stearate (2.5 mg) are mixed and formulated into granules. Fine crystalline cellulose (10 mg) and magnesium stearate (2.5 mg) are added to the granules, mixed and formulated into a tablet under pressure.

Example of pharmaceutical substance 3

The compound (10 mg) prepared in Example 16, inositol (100 mg), and benzyl alcohol (20 mg) are dissolved in distilled water for injection so that the whole volume becomes 2 ml, and placed in an ampoule. All operations are carried out under a sterilized condition.

Example of pharmaceutical substance 4

The compound (10 mg) prepared in Example 16, lactose (35 mg), corn starch (150 mg), fine crystalline cellulose (20 mg) and magnesium stearate (2.5 mg) are mixed and formulated into granules. Fine crystalline cellulose (1Omg) and magnesium stearate (2.5 mg) are added to the granules, mixed and formulated into a tablet under pressure.

Test Example 1

Osteogenesis promoting effect:

Using the stromal cells prepared from the femur bone marrow of a normal rat, an alkaline phosphatase activity was measured as an index of osteogenesis. Briefly, according to the method of Maniatopoulos et al. [Cell Tissue Research, volume 254, p.317 (1998)], the stromal cells were prepared from the femur bone of a Sprague-Dawley male rat, 7 weeks of age, and cultured in an α-MEM (minimum essential medium) solution containing dexamethasone ($10^{-7}$M) and β-glycerophosphoric acid ($10^{-2}$M) in order to generate calcified bony tissue. One week later, the confluent primary cells were treated with 0.25% trypsin-0.25% EDTA solution, recovered, and subclutured on a culture plate at a cell density of $1.6\times10^{-4}$ cells/cm$^{-2}$, (cultured day 0). From the 2$^{nd}$ day of the culture, a test compound ($10^{-5}$M) was added to the above culture medium, and cultured for an additional 5 days. The cells were washed with a phosphate buffer, and after addition of 0.2% Nonidet P-40, they were homogenized and centrifuged at 3000 rpm for 10 minutes. The supernatant was measured for an alkaline phosphatase activity according to the method of Lowry et al. [Journal of Biological Chemistry, volume 207, p.19 (1954)]. Tables 1 and 2 show the measured values in terms of mean±standard error (SE). Statistical analysis was performed by means of the Student's t-test.

TABLE 1

| Compound | Concentration (M) | Alkaline phosphatase activity (A$_{405}$) |
| --- | --- | --- |
| Example no. 1 | $10^{-5}$ | 0.564 ± 0.041** |
| Example no. 2 | $10^{-5}$ | 0.310 ± 0.008** |
| Example no. 5 | $10^{-5}$ | 0.558 ± 0.040** |
| Control | No addition | 0.175 ± 0.009 |

Mean ± S.E.. (n = 4), **p < 0.01 vs control (Student's t-test)

TABLE 2

| Compound | Concentration (M) | alkaline phosphatase activity ($A_{405}$) |
|---|---|---|
| Example no. 16 | $10^{-5}$ | 0.720 ± 0.033** |
| Example no. 18 | $10^{-5}$ | 0.720 ± 0.037 |
| Control | No addition | 0.180 ± 0.008 |

Mean ± S.E.. (n = 4), **p < 0.01 vs control (Student's t-test)

From table 1 and 2, it is found that the test compounds have an excellent osteogenesis promoting effect.

Industrial Applicability

Compounds (I) of the present invention have a potent osteogenesis promoting effect, chondrogenesis promoting effect, cartilage destruction suppressing effect, and cartilage cell differentiation promoting effect, and are superior in clinically useful characteristics such as stability, absorption (particularly, oral absorption), bioavailability, and the like. They, accordingly, can be used in prevention and treatment of bone diseases or chondropathy, for example, osteoporosis, fracture, cartilage defect, chronic rheumatoid arthritis, involving a cartilage, and osteoarthritis involving a cartilage.

We claim:

1. A compound of the formula:

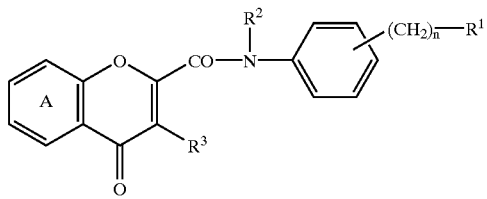

wherein the ring A is an optionally substituted benzene ring which may be substituted by 1 to 3 substituents selected from the group consisting of
hydroxy,
acyloxy,
mercapto,
halogen atom,
$C_{1-10}$ alkyl,
$C_{1-10}$ alkoxy,
$C_{1-10}$ alkylthio and
alkylenedioxy of the formula: —O—$(CH_2)$m—O—, wherein m is an integer of 1–4;

$R^1$ is an optionally substituted non-aromatic heterocyclic group,
wherein said non-aromatic heterocyclic group is a 5- to 7-membered non-aromatic heterocyclic group containing from 1 to 4 heteroatoms selected from the group consisting of nitrogen atom, sulfur atom and oxygen atom,
and wherein optional substituents of said non-aromatic heterocyclic group are 1 to 4 substituents selected from the group consisting of halogen atom, hydroxy, oxo, $C_{1-10}$ alkyl, $C_{10-6}$ alkoxy, $C_{1-6}$ acyl, amino, mono- or di-$C_{1-6}$ alkylamino, $C_{1-6}$ alkylsulfonyl, carboxy, $C_{1-6}$ alkoxy-carbonyl and phosphono;

$R^2$ is a hydrogen atom or a hydrocarbon group;

$R^3$ is a hydrogen atom, a hydrocarbon group or halogen;

n is an integer of 0 to 3;
or a salt thereof;
or a prodrug thereof.

2. A compound according to claim 1, wherein $R^2$ is a hydrogen atom or a $C_{1-6}$ alkyl; and $R^3$ is a hydrogen atom; or a salt thereof.

3. A compound according to claim 1, wherein the substructure containing the ring A is represented by the formula:

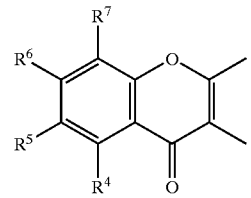

wherein $R^4$ is a hydrogen atom or a hydroxy group, each of $R^5$ to $R^7$ may be same or different and each is a hydrogen atom, a halogen atom, a $C_{1-10}$ alkyl or a $C_{1-10}$ alkoxy, $R^2$ is a hydrogen atom or a $C_{1-6}$ alkyl group; $R^3$ is a hydrogen atom, or a salt thereof.

4. A compound according to claim 1, wherein the 5- to 7-membered non-aromatic heterocyclic group of the optionally substituted 5- to 7-membered non-aromatic heterocyclic group is one containing at least 1 nitrogen atom, or a salt thereof.

5. A compound according to claim 4, wherein the 5- to 7-membered non-aromatic heterocyclic group of the optionally substituted 5- to 7-membered non-aromatic heterocyclic group is pyrrolidine, imidazolidine, thiazolidine, isothiazolidine, oxazolidine, oxadiazolidine, piperidine, piperazine, thiomorpholine or morpholine, or a salt thereof.

6. A compound according to claim 3, wherein $R^2$ is a hydrogen atom and $R^4$ is a hydroxy group, or a salt thereof.

7. A compound according to claim 3, wherein $R^2$ and $R^4$ are each a hydrogen atom, or a salt thereof.

8. N-4-(2,4-dioxothiazolidin-5-yl)methyl]phenyl]-4-oxo-4H-1-benzopyran-2-carboxamide, N-[4-[(2,4-dioxo-oxazolidin-5-yl)methyl]phenyl]-4-oxo-4H-1-benzopyran-2-carboxamide, N-[4-[(4-morpholinyl)methyl]phenyl]-4-oxo-4H-1-benzopyran-2-carboxamide, 5,7-dihydroxy-N-[4-(2,4-dioxothiazolidin-5-yl)methyl]phenyl]-4-oxo-4H-1-benzopyran-2-carboxamide, N-[4-[2,4-dioxothiazolidin-5-yl]methyl]phenyl]-5-hydroxy-7-methoxy-4-oxo-4H-1-benzopyran-2-carboxamide, 5,7-dihydroxy-N-[4-[(4-morpholinyl)methyl]phenyl]-4-oxo-4H-1-benzopyran-2-carboxamide, 5-hydroxy-N-[4-[(4-morpholinyl)methyl]phenyl]-4-oxo-4H-1-benzopyran-2-carboxamide, N-[4-[(2-oxazolidon-3-yl)methyl]phenyl]-4-oxo-4H-1-benzopyran-2-carboxamide, N-[4-(2,6-dioxo-1-piperidinyl)methyl]phenyl]-4-oxo-4H-1-benzopyran-2-carboxamide, N-[4-(2,4-dioxo-oxazolidin-5-yl)methyl]phenyl]-5-hydroxy-4-oxo-4H-1-benzopyran-2-carboxamide, 5-hydroxy-N-methyl-N-[4-(4-morpholinyl)methyl]phenyl]-4-oxo-4H-1-benzopyran-2-carboxamide, or 4-oxo-N-[4-[(4-oxo-1-piperidinyl)methyl]phenyl]-4H-1-benzopyran-2-carboxamide, or a salt thereof.

9. A process for producing chromone derivatives of the formula:

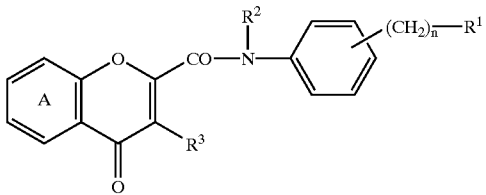

wherein the ring A is an optionally substituted benzene ring which may be substituted by 1 to 3 substituents selected from the group consisting of hydroxy,
acyloxy,
mercapto,
halogen atom,
$C_{1-10}$ alkyl,
$C_{1-10}$ alkoxy,
$C_{1-10}$ alkylthio and
alkylenedioxy of the formula: —O—$(CH_2)$m—O—,
wherein m is an integer of 1–4;

$R^1$ is an optionally substituted non-aromatic heterocyclic group,
wherein said non-aromatic heterocyclic group is a 5- to 7-membered non-aromatic heterocyclic group containing from 1 to 4 heteroatoms selected from the group consisting of nitrogen atom, sulfur atom and oxygen atom,
and wherein optional substituents of said non-aromatic heterocyclic group are 1 to 4 substituents selected from the group consisting of halogen atom, hydroxy, oxo, $C_{1-10}$ alkyl, $C_{1-6}$ alkoxy, $C_{1-6}$ acyl, amino, mono- or di-$C_{1-6}$ alkylamino, $C_{1-6}$ alkylsulfonyl, carboxy, $C_{1-6}$ alkoxy-carbonyl and phosphono;

$R^2$ is a hydrogen atom or a hydrocarbon group;

$R^3$ is a hydrogen atom, a hydrocarbon group, or a halogen;

and n is an integer of 0–3;

or a salt thereof, which comprises reacting a compound of the formula:

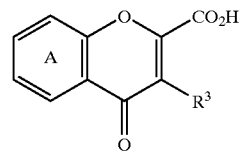

wherein each symbol has the same meaning as mentioned above;

or a reactive derivative at the carboxy group thereof or a salt thereof, with a compound of the formula:

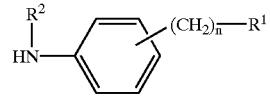

wherein each symbol has the same meaning as mentioned above;

or a reactive derivative at the amino group thereof
or a salt thereof.

10. 5,6-methylenedioxy-4-oxo-4H-1-benzopyran-2-carboxylic acid, 5,6-dihydroxy-4-oxo-4H-1-benzopyran-2-carboxylic acid, or 5-hydroxy-7-methyl-4-oxo-4H-1-benzopyran-2-carboxylic acid; or a salt thereof.

11. A pharmaceutical composition which comprises a compound of the formula:

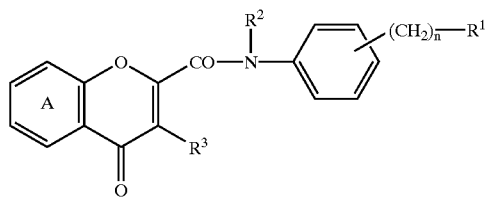

wherein the ring A is an optionally substituted benzene ring which may be substituted by 1 to 3 substituents selected from the group consisting of
hydroxy,
acyloxy,
mercapto,
halogen atom,
$C_{1-10}$ alkyl,
$C_{1-10}$ alkoxy,
$C_{1-10}$ alkylthio and
alkylenedioxy of the formula: —O—$(CH_2)$m—O—,
wherein m is an integer of 1–4;

$R^1$ is an optionally substituted non-aromatic heterocyclic group,
wherein said non-aromatic heterocyclic group is a 5- to 7-membered non-aromatic heterocyclic group containing from 1 to 4 heteroatoms selected from the group consisting of nitrogen atom, sulfur atom and oxygen atom,
and wherein optional substituents of said non-aromatic heterocyclic group are 1 to 4 substituents selected from the group consisting of halogen atom, hydroxy, oxo, $C_{1-10}$ alkyl, $C_{1-6}$ alkoxy, $C_{1-6}$ acyl, amino, mono- or di-$C_{1-6}$ alkylamino, $C_{1-6}$ alkylsulfonyl, carboxy, $C_{1-6}$ alkoxy-carbonyl and phosphono;

$R^2$ is a hydrogen atom or a hydrocarbon group, $R^3$ is a hydrogen atom, a hydrocarbon group, or halogen;

and n is an integer of 0–3;

or a salt thereof;
and a pharmaceutically acceptable carrier.

12. A pharmaceutical composition according to claim 11, which is an osteogenesis promoting agent.

13. A pharmaceutical composition according to claim 11, which is a preventive or therapeutic agent for bone disease.

14. A pharmaceutical composition according to claim 11, which is a preventive or therapeutic agent for fracture.

15. A pharmaceutical composition according to claim 11, which is a preventive or therapeutic agent for chondropathy.

16. A pharmaceutical composition which comprises a compound of the formula:

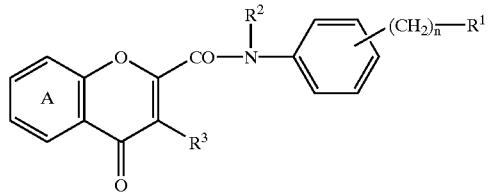

wherein the ring A is an optionally substituted benzene ring which may be substituted by 1 to 3 substituents selected from the group consisting of
hydroxy,
acyloxy,
mercapto, halogen atom, $C_{1-10}$ alkyl, $C_{1-10}$ alkoxy, $C_{1-10}$ alkylthio and alkylenedioxy of the formula: —O—$(CH_2)$m—O—, wherein m is an integer of 1–4;

$R^1$ is an optionally substituted non-aromatic heterocyclic group, wherein said non-aromatic heterocyclic group is a 5- to 7-membered non-aromatic heterocyclic group containing from 1 to 4 heteroatoms selected from the group consisting of nitrogen atom, sulfur atom and oxygen atom, and wherein optional substituents of said non-aromatic heterocyclic group are 1 to 4 substituents selected from the group consisting of halogen atom, hydroxy, oxo, $C_{1-10}$ alkyl, $C_{1-6}$ alkoxy, $C_{1-6}$ acyl, amino, mono- or di-$C_{1-6}$ alkylamino, $C_{1-6}$ alkylsulfonyl, carboxy, $C_{1-6}$ alkoxy-carbonyl and phosphono;

$R^2$ is a hydrogen atom or a hydrocarbon group;

$R^3$ is a hydrogen atom, a hydrocarbon group or halogen;

n is an integer of 0 to 3;

or a salt thereof or a prodrug thereof;

and a pharmaceutically acceptable carrier.

17. A method for promoting osteogenesis which comprises administering a compound according to claim 1 or a salt thereof to a mammal in need thereof.

18. A method for manufacturing an osteogenesis promoting agent comprising combining a compound of the formula:

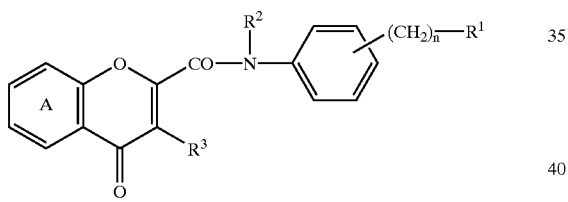

wherein the ring A is an optionally substituted benzene ring which may be substituted by 1 to 3 substituents selected from the group consisting of hydroxy, acyloxy, mercapto, halogen atom, $C_{1-10}$ alkyl, $C_{1-10}$ alkoxy, $C_{1-10}$ alkylthio and alkylenedioxy of the formula: —O—$(CH_2)$m—O—, wherein m is an integer of 1–4;

$R^1$ is an optionally substituted non-aromatic heterocyclic group, wherein said non-aromatic heterocyclic group is a 5- to 7-membered non-aromatic heterocyclic group containing from 1 to 4 heteroatoms selected from the group consisting of nitrogen atom, sulfur atom and oxygen atom, and wherein optional substituents of said non-aromatic heterocyclic group are 1 to 4 substituents selected from the group consisting of halogen atom, hydroxy, oxo, $C_{1-10}$ alkyl, $C_{1-6}$ alkoxy, $C_{1-6}$ acyl, amino, mono- or di-$C_{1-6}$ alkylamino, $C_{1-6}$ alkylsulfonyl, carboxy, $C_{1-6}$ alkoxy-carbonyl and phosphono;

$R^1$ is a hydrogen atom or a hydrocarbon group, $R^1$ is a hydrogen atom, a hydrocarbon group, or halogen;

and n is an integer of 0–3;

or a salt thereof;

with a pharmaceutically acceptable carrier.

* * * * *